(12) United States Patent
Fukuhara et al.

(10) Patent No.: US 11,819,091 B2
(45) Date of Patent: Nov. 21, 2023

(54) METHOD FOR MANUFACTURING MOLDED SURFACE FASTENER AND MOLDED SURFACE FASTENER

(71) Applicant: YKK Corporation, Tokyo (JP)

(72) Inventors: Yoshiyuki Fukuhara, Kurobe (JP); Hiroyuki Yamashita, Kurobe (JP); Takahiro Fuse, Kurobe (JP); Kyoichi Yuki, Kurobe (JP); Ryosuke Tanimoto, Kurobe (JP)

(73) Assignee: YKK Corporation, Tokyo (JP)

( * ) Notice: Subject to any disclaimer, the term of this patent is extended or adjusted under 35 U.S.C. 154(b) by 409 days.

(21) Appl. No.: 17/291,146

(22) PCT Filed: Nov. 16, 2018

(86) PCT No.: PCT/JP2018/042457
§ 371 (c)(1),
(2) Date: May 4, 2021

(87) PCT Pub. No.: WO2020/100282
PCT Pub. Date: May 22, 2020

(65) Prior Publication Data
US 2022/0039521 A1    Feb. 10, 2022

(51) Int. Cl.
*A44B 1/08* (2006.01)
*B29C 41/26* (2006.01)
(Continued)

(52) U.S. Cl.
CPC ............ *A44B 1/08* (2013.01); *B29C 41/26* (2013.01); *B29C 43/24* (2013.01); *B29K 2101/12* (2013.01); *B29L 2031/727* (2013.01)

(58) Field of Classification Search
CPC ... A44B 1/08; A44B 18/0065; A44B 18/0049; B29C 41/26; B29C 43/24; B29C 48/022;
(Continued)

(56) References Cited

U.S. PATENT DOCUMENTS 5,679,302 A      10/1997  Miller et al.
5,749,129 A *     5/1998  Murasaki ........... A44B 18/0049
                                                24/442
(Continued)

FOREIGN PATENT DOCUMENTS

CN          1956832 A       5/2007
CN        101437418 A       5/2009
(Continued)

OTHER PUBLICATIONS

Office Action, Taiwanese Patent Application No. 108110652, dated Sep. 3, 2019.
(Continued)

*Primary Examiner* — David M Upchurch
(74) *Attorney, Agent, or Firm* — Kilpatrick Townsend & Stockton LLP

(57) ABSTRACT

A method for manufacturing a molded surface fastener may include using, as a synthetic resin forming the molded surface fastener, a thermoplastic resin having a melt flow rate of 20 g/10 min or more and 60 g/10 min or less and a flexural modulus of 1000 MPa or more and 2300 MPa or less. Consequently, an engaging element in which a top end surface of an engaging head portion is flat, and at least a part of a back-side proximal end surface of the engaging head portion has an angle of 70° or more and 110° or less with respect to a height direction of the stem portion can be stably molded, and thus the molded surface fastener that has a high peel strength and a good texture can be obtained.

7 Claims, 10 Drawing Sheets

(51) Int. Cl.
*B29C 43/24* (2006.01)
*B29K 101/12* (2006.01)
*B29L 31/00* (2006.01)

(58) Field of Classification Search
CPC ......... B29C 48/35; B29C 43/46; B29C 43/52; B29C 48/001; B29C 48/0011; B29C 48/002; B29C 43/26; B29C 43/003; B29C 43/222; B29K 2101/12; B29L 2031/727; B29L 2031/729; A61F 13/625
See application file for complete search history.

(56) References Cited

U.S. PATENT DOCUMENTS

| | | |
|---|---|---|
| 5,868,987 A | 2/1999 | Kampfer et al. |
| 2003/0126724 A1 | 7/2003 | Kono et al. |
| 2005/0202205 A1 | 9/2005 | Petersen et al. |
| 2006/0096071 A1 | 5/2006 | Pacione et al. |
| 2008/0272512 A1 | 11/2008 | Clune |
| 2009/0126166 A1 | 5/2009 | Tuma |
| 2012/0151722 A1 | 6/2012 | Hertlein et al. |
| 2016/0128435 A1 | 5/2016 | Fukuzawa et al. |
| 2016/0331085 A1* | 11/2016 | Mizumoto ......... A44B 18/0049 |
| 2018/0360170 A1 | 12/2018 | Fukuhara et al. |
| 2018/0368534 A1 | 12/2018 | Fukuhara et al. |
| 2019/0008239 A1 | 1/2019 | Fukuhara et al. |
| 2019/0059523 A1 | 2/2019 | Fukuzawa et al. |
| 2020/0196715 A1 | 6/2020 | Fukuhara et al. |
| 2020/0196716 A1 | 6/2020 | Fukuhara et al. |
| 2021/0106101 A1 | 4/2021 | Fukuhara et al. |

FOREIGN PATENT DOCUMENTS

| | | |
|---|---|---|
| EP | 3395193 A1 | 10/2018 |
| JP | 3515117 B2 | 1/2004 |
| JP | 2006-518288 A | 8/2006 |
| JP | 4168182 B2 | 8/2008 |
| JP | 2010-110537 A | 5/2010 |
| JP | 2014-501588 A | 1/2014 |
| TW | 200301685 A | 7/2003 |
| TW | 201616997 A | 5/2016 |
| TW | 201726021 A | 8/2017 |
| WO | 2017/110127 A1 | 6/2017 |
| WO | 2017/168757 A1 | 10/2017 |

OTHER PUBLICATIONS

Decision of Refusal, Taiwanese Patent Application No. 108110652, dated Jun. 11, 2020.
European Extended Search Report, European Patent Application No. 18940090.6, dated Oct. 18, 2021, 10 pages.
International Search Report, PCT Patent Application No. PCT/JP2018/042457, dated Feb. 5, 2019.
Office Action, European Patent Application No. 18940090.6, dated Feb. 8, 2023, 4 pages.
Office Action, Chinese Patent Application No. 201880099299.7, dated May 23, 2022, 15 pages.
Decision of Refusal, Chinese Patent Application No. 201880099299.7, dated Jan. 19, 2023, 9 pages.

* cited by examiner

METHOD FOR MANUFACTURING MOLDED SURFACE FASTENER AND MOLDED SURFACE FASTENER

TECHNICAL FIELD

The invention relates to a method for manufacturing a molded surface fastener having a plurality of engaging elements provided on a base portion, and a molded surface fastener manufactured by the manufacturing method.

BACKGROUND ART

Conventionally, there has been known surface fastener products in which a loop member (female surface fastener) having a plurality of loops and a male molded surface fastener that is attachable to and detachable from the loop member are used as a pair. In the male molded surface fastener manufactured by, for example, molding a synthetic resin, a plurality of male engaging elements with a mushroom shape or the like are provided upright on the upper surface of a flat plate-like base portion.

The surface fastener product having such a male surface fastener is currently used for a wide variety of commercial products including products attached to and detached from the human body such as disposable diapers, infant diaper covers, supporters for protecting limb joints, lumber corsets (back support belts), and gloves.

Further, an example of a method for manufacturing a surface fastener having a plurality of male engaging elements with a mushroom shape or a J-shape is described in, for example, JP 3515117 B1 (Patent Document 1 corresponding to JP 8-508910 A) or JP 4168182 B1 (Patent Document 2 corresponding to JP 2002-504006 A).

In the manufacturing methods described in Patent Document 1 and Patent Document 2, a primary molding step of molding a primary molded body having a flat plate-like base portion and a plurality of primary stem portions (temporary elements) that are provided upright on the base portion is performed first. Thereafter, a secondary molding step is performed, in which the resultant primary molded body is caused to pass between calendar rolls (heat-press rolls), which are vertically paired, so that a part of the primary stem portions formed in the primary molded body are hated and pressed.

With this secondary molding step, the primary stem portion (temporary element) is transformed into a mushroom-shaped engaging element having a stem portion and an engaging head portion integrally formed on the stem portion, or a J-shaped engaging element having a stem portion and an engaging head portion bent to extend from the upper end portion of the stem portion. As a result, it is possible to easily manufacture a surface fastener including a plurality of engaging elements with a predetermined shape.

Particularly in the manufacturing method of Patent Document 1, as the set speed at which the primary molded body is inserted, the dimension of a gap for inserting the primary molded body between the upper and lower calendar rolls, and the heating capacity of a calendar roll surface are controlled in the secondary molding step, it is possible to manufacture a surface fastener having a plurality of mushroom-shaped engaging elements in which the top end surface (upper end surface) of an engaging head portion is formed in a slightly recessed shape. Patent Document 1 describes that as the engaging element has the shape described above, excellent engagement force in a shear direction with the loop member can be achieved and low-cost manufacturing can also be achieved.

In the manufacturing method of Patent Document 2, the surface of the upper calendar roll used in the secondary molding step includes a plurality of recessed grooves (valleys) formed along one direction. As the secondary molding step is performed by using such a calendar roll having the plurality of recessed grooves, it is possible to manufacture a surface fastener having a plurality of engaging elements bent in a J-shape or a plurality of engaging elements in which the engaging head portion is formed long in a machine direction and a plurality of linear recesses are formed on the top end surface (upper end surface) of the engaging head portion from the first stem portions of the primary molded body. Patent Document 2 describes that as the calendar roll in the secondary molding step has a plurality of recessed grooves, it is possible to obtain an engaging element that has increased engagement with the loop member.

CITATION LIST

Patent Document

Patent Document 1: JP 3515117 B1
Patent Document 2: JP 4168182 B1

SUMMARY OF INVENTION

Technical Problem

As described above, in the manufacturing methods of Patent Document 1 and Patent Document 2, as specific molding conditions and specific shapes of calendar roll are adopted in the secondary molding step, an engaging element (in particular, engaging head portion) is formed in a characteristic shape, and thus the peel strength (engagement strength) of a molded surface fastener with respect to a loop member is improved. However, surface faster products are currently used for a variety of commercial products as described above, and some commercial products may require higher strength. Consequently, it is necessary to develop a molded surface fastener that has higher peel strength with respect to the loop member.

In addition, in the molded surface fastener manufactured by the manufacturing method of Patent Document 1 or Patent Document 2, the upper end surface of each engaging element is not formed flat. For this reason, the upper surface side of the molded surface fastener, on which a plurality of engaging elements are provided, hardly has a good texture (good touch feeling), and thus there is still a room for improvement.

The invention has been made in view of the above conventional problems, and an object of the invention is to provide a method for manufacturing a molded surface fastener by which it is possible to form an engaging element in a shape capable of easily obtaining high peel strength and achieving a good texture on the upper surface side of the fastener, and a molded surface fastener manufactured by the manufacturing method.

Solution to Problem

In order to achieve the above object, a method for manufacturing a molded surface fastener according to a first embodiment of the invention is a method for manufacturing a molded surface fastener that is made of a synthetic resin and has a plurality of engaging elements each of which includes a stem portion standing from a base portion and an engaging head portion integrally formed on the stem portion, the method including a primary molding step of molding a primary molded body having the base portion and a plurality of temporary elements provided upright on the base portion and a secondary molding step of heating at least a part of each of the temporary elements of the primary molded body and pressing the temporary elements from above to mold the molded surface fastener, being characterized in that the method comprises using a thermoplastic resin having a melt flow rate of 20 g/10 min or more and 60 g/10 min or less and a flexural modulus of 1000 MPa or more and 2300 MPa or less as the synthetic resin.

A method for manufacturing a molded surface fastener according to a second embodiment of the invention is a method for manufacturing a molded surface fastener that is made of a synthetic resin and has a plurality of engaging elements each of which includes a stem portion standing from a base portion and an engaging head portion that has a disc shape and is integrally formed on the stem portion, the method including a primary molding step of molding a primary molded body having the base portion and a plurality of temporary elements provided upright on the base portion and a secondary molding step of heating at least a part of each of the temporary elements of the primary molded body and pressing the temporary elements from above to mold the molded surface fastener, being characterized in that the method comprises using a thermoplastic resin having a melt flow rate of 1 g/10 min or more and 60 g/10 min or less and a flexural modulus of 1600 MPa or more and 3000 MPa or less as the synthetic resin, and pressing the temporary elements from above by a pressing roller with a diameter of 300 mm or more and 500 mm or less in the secondary molding step.

Further, in the method for manufacturing a molded surface fastener according to the first and second embodiments, the method preferably comprises molding the engaging element whose height dimension is less than the height dimension of the temporary element by 20 μm or more and 80 μm or less by heating at least a part of the temporary element at a heating temperature that is a first temperature or higher, the first temperature being lower than a melting point of the synthetic resin by 50° C., and a second temperature or lower, the second temperature being lower than the melting point of the synthetic resin by 20° C., and pressing the temporary element from above in the secondary molding step.

Next, a molded surface fastener according to the first embodiment of the invention is a molded surface fastener that is made of a synthetic resin and has a plurality of engaging elements each of which includes a stem portion standing from a base portion and an engaging head portion integrally formed on the stem portion, being characterized in that the engaging head portion has at least a top end surface that is exposed upward and formed flat and a back-side proximal end surface that is disposed on an opposite side to the top end surface and extends outward from a boundary portion with the stem portion, and at least a part of the back-side proximal end surface of the engaging head portion has an angle of 70° or more and 110° or less with respect to a height direction of the stem portion.

Further, in the molded surface fastener according to the first embodiment, the engaging head portion preferably has a circular shape in a plan view of the molded surface fastener, at least a part of the back-side proximal end surface of the engaging head portion preferably has a plane that shows a straight line when a cross-section that is parallel to a height direction of the engaging element and includes a central axis of the stem portion is viewed in the engaging element, and the plane of the back-side proximal end surface preferably has a length of 20 μm or more in the cross-section.

A molded surface fastener according to the second embodiment of the invention is a molded surface fastener that is made of a synthetic resin and has a plurality of engaging elements each of which includes a stem portion standing from a base portion and an engaging head portion integrally formed on the stem portion, being characterized in that the engaging head portion has at least a top end surface that is exposed upward and a back-side proximal end surface that is disposed on an opposite side to the top end surface and extends outward from a boundary portion with the stem portion, and the engaging head portion has an elliptical shape in a plan view of the molded surface fastener, and at least a part of the back-side proximal end surface of the engaging head portion has an angle of 120° or more with respect to a height direction of the stem portion.

Advantageous Effects of Invention

The inventors have diligently studied a method for manufacturing a molded surface fastener in order to obtain a shape of an engaging element that increases the peel strength of a molded surface fastener to be manufactured and also improves a texture on the upper surface side of the molded surface fastener. As a result, the inventors have found that among the various properties of synthetic resins forming the molded surface fastener, a melt flow rate (hereinafter, sometimes abbreviated as "MFR") and a flexural modulus are important, and these properties significantly influence the shape of the engaging element, and have completed the invention by repeating experiments and studies.

That is, the method for manufacturing a molded surface fastener according to the first embodiment of the invention includes the primary molding step of molding the primary molded body having the base portion and a plurality of the temporary elements provided upright on the base portion and the secondary molding step of heating at least a part of each of the temporary elements of the primary molded body obtained and pressing the temporary elements from above to mold the molded surface fastener. Further, in the manufacturing method according to the first embodiment, a thermoplastic resin having an MFR of 20 g/10 min or more and 60 g/10 min or less, preferably 40 g/10 min or more and 60 g/10 min or less and a flexural modulus of 1000 MPa or more and 2300 MPa or less, preferably 1000 MPa or more and 1500 MPa or less is used as the synthetic resin (material) forming the molded surface fastener.

Since the molded surface fastener is molded by using the thermoplastic resin with an MFR and flexural modulus within the range described above, it is possible to smoothly and stably manufacture the molded surface fastener having a plurality of engaging elements in which a thin and flat engaging head portion is provided, and the back-side proximal end surface of the engaging head portion extending outward from the stem portion is formed to make an angle of 70° or more and 110° or less with respect to a vertical direction.

Since each engaging element of the molded surface fastener manufactured has the characteristic shape described above, when a loop member is engaged with the molded surface fastener, loops caught on the engaging head portion of the engaging element can be hardly removed (can hardly come off) from the engaging element. As a result, the peel strength (engagement strength) of the molded surface fastener with respect to the loop member can be easily enhanced. Further, since the top end surface of the engaging head portion can be made flat, the molded surface fastener can achieve a good texture on the upper surface side of the fastener.

Next, in the method for manufacturing a molded surface fastener according to the second embodiment of the invention, the primary molding step and the secondary molding step are performed, and a thermoplastic resin having an MFR of 1 g/10 min or more and 60 g/10 min or less and a flexural modulus of 1600 MPa or more and 3000 MPa or less is used as the synthetic resin (material) forming the molded surface fastener. Further, in the manufacturing method according to the second embodiment, in the secondary molding step, the temporary element is pressed from above by the pressing roller that has a diameter of 300 mm or more and 500 mm or less and is capable of heating a roller surface to a predetermined temperature.

Since the molded surface fastener is molded by using the thermoplastic resin with an MFR and flexural modulus within the range described above and the pressing roller with a diameter of 300 mm or more and 500 mm or less is used in the secondary molding step, it is possible to smoothly and stably manufacture the molded surface fastener having a plurality of engaging elements in which a thin engaging head portion that has an elliptical shape in the plan view of the molded surface fastener is provided, and the back-side proximal end surface of the engaging head portion extending outward from the stem portion is formed to make an angle of 120° or more with respect to the vertical direction.

Since each engaging element of the molded surface fastener manufactured has the characteristic shape described above, when the loop member is engaged with the molded surface fastener, the loops caught on the engaging head portion of the engaging element can be hardly removed from the engaging element. As a result, the peel strength (engagement strength) of the molded surface fastener with respect to the loop member can be easily enhanced. Further, since the top end surface of the engaging head portion can be made flat, the molded surface fastener with a good texture can be obtained.

In the manufacturing method according to the first and second embodiments of the invention, the secondary molding step includes heating at least a part of the temporary element at a heating temperature that is a first temperature or higher, the first temperature being lower than the melting point of the synthetic resin by 50° C., and a second temperature or lower, the second temperature being lower than the melting point of the synthetic resin by 20° C., and pressing the temporary element from above to mold the engaging element whose height dimension is less than the height dimension of the temporary element by 20 μm or more and 80 μm or less. By performing the secondary molding step (secondary processing) under such conditions, the engaging head portion of each engaging element can be formed more stably in the characteristic shape of the first or second embodiment as described above.

The molded surface fastener according to the first embodiment of the invention has a plurality of the engaging elements each of which includes the stem portion standing from the base portion and the engaging head portion that has a disc shape and is integrally formed on the stem portion. Further, the engaging head portion at least has the top end surface that is exposed upward and formed flat and a back-side proximal end surface that has a donut shape, is disposed so as to face the base portion on the opposite side to the top end surface in the upper-lowerl direction, and extends outward from the boundary portion with the stem portion, and at least a part of the back-side proximal end surface of the engaging head portion has an angle of 70° or more and 110° or less, preferably 70° or more and 90° or less with respect to the height direction (upper-lowerl direction) of the stem portion.

In the molded surface fastener having the engaging element described above, since the back-side proximal end surface disposed on the engaging head portion is formed at an angle within a predetermined range with respect to the upper-lowerl direction, when a plurality of loops of the loop member are engaged with the molded surface fastener, the loops caught on the engaging head portion of the engaging element can be hardly removed from the engaging element. As a result, the molded surface fastener according to the invention can have a high peel strength with respect to the loop member. Further, since the top end surface of the engaging head portion is made flat, the molded surface fastener with a good texture can be obtained.

Moreover, in the molded surface fastener according to the first embodiment, the engaging head portion of the engaging element has a circular shape in the plan view of the molded surface fastener, and at least a part of the back-side proximal end surface of the engaging head portion has a plane that is a straight line when the cross-section of the engaging element that is parallel to the height direction of the engaging element and includes the central axis of the stem portion is viewed. In this case, the plane of the back-side proximal end surface has a length of 20 μm or more, preferably 40 μm or more in the cross-sectional view described above.

For example, most loops of loop members generally used for disposable diapers, diaper covers, and the like have a thickness of about 10 μm to 15 μm, but in the first embodiment, the engaging head portion is circular in a plan view and the plane of the back-side proximal end surface has a length of 20 μm or more as described above, and thus the loops of the loop member, which is common in disposable diapers, can be easily caught on the disc-shaped engaging head portion of the engaging element. Further, since the caught loops can be stably held by the engaging element, the loops can be hardly removed from the engaging element.

In this case, the plane of the back-side proximal end surface of the engaging head portion preferably has a length of 90 μm or less in the cross-sectional view described above. As a result, it is possible to prevent the engaging head portion from becoming too large, and the loop member can be smoothly engaged with the molded surface fastener.

The molded surface fastener according to the second embodiment of the invention has a plurality of the engaging elements each of which includes the stem portion standing from the base portion and the engaging head portion that has a disc shape and is integrally formed on the stem portion. Further, the engaging head portion at least has the top end surface that is exposed upward and formed flat and the back-side proximal end surface that has a donut shape, is disposed so as to face the base portion on the opposite side to the top end surface in the upper-lowerl direction, and extends outward from the boundary portion with the stem portion, and the engaging head portion has an elliptical shape in the plan view of the molded surface fastener. Further, at least a part of the back-side proximal end surface of the engaging head portion has an angle of 120° or more with respect to the height direction (upper-lowerl direction) of the stem portion.

In the molded surface fastener having the engaging element described above, since the back-side proximal end surface disposed on the engaging head portion is formed at an angle of 120° or more with respect to the upper-lowerl direction, the flat top end surface of the engaging head portion is easily formed in a wide area. Consequently, a good texture on the upper surface side of the fastener can be achieved in the molded surface fastener. Further, the back-side proximal end surface of the engaging head portion is formed at an angle described above, but the engaging head portion has an elliptical shape in the plan view of the molded surface fastener, and thus when a plurality of loops of the loop member are engaged with the molded surface fastener, the loops caught on the engaging head portion of the engaging element can be hardly removed from the engaging element in the major axis side portion of the engaging head portion. As a result, the molded surface fastener according to the invention can have a high peel strength with respect to the loop member.

DESCRIPTION OF EMBODIMENTS

Hereinafter, preferred embodiments of the invention will be described in detail with reference to the drawings. The invention is not limited to the embodiments to be described below, and various changes can be made as long as they have substantially the same configuration as the invention and exhibit similar effects to the invention. For example, in each of the following examples, the number, arrangement position, and formation density of engaging elements arranged on a base portion of a molded surface fastener are not particularly limited, and can be freely changed.

First Embodiment

Figure 1:
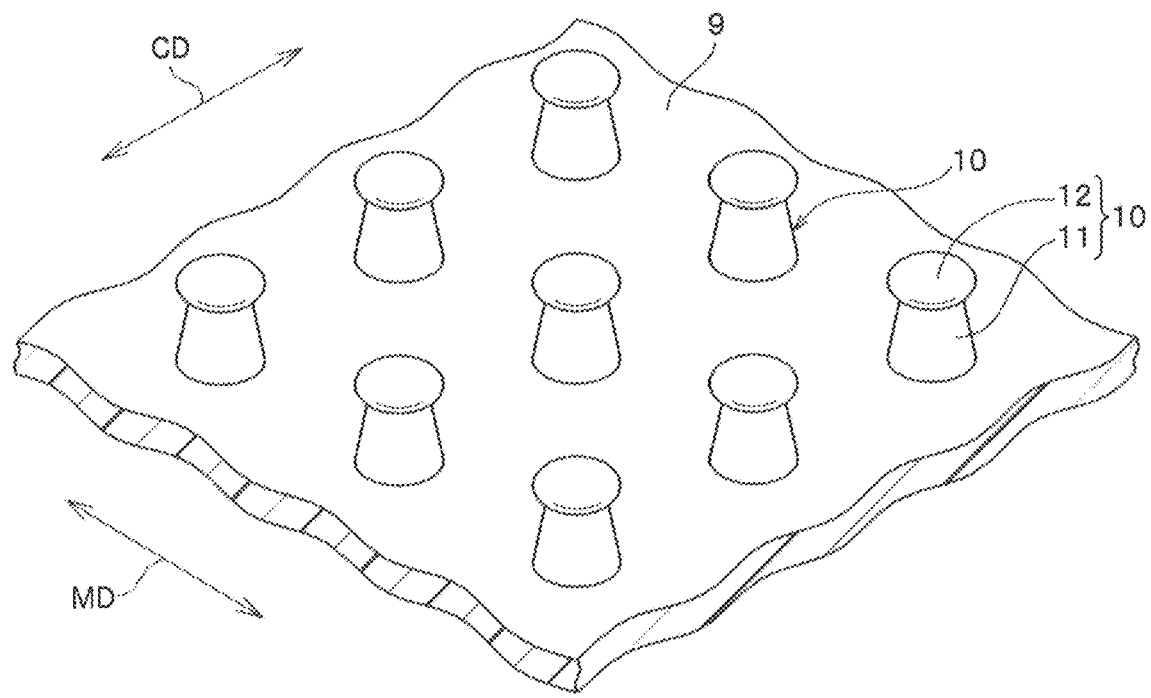
FIG. 1 is a perspective view illustrating a molded surface fastener according to a first embodiment of the invention.
Figure 2:
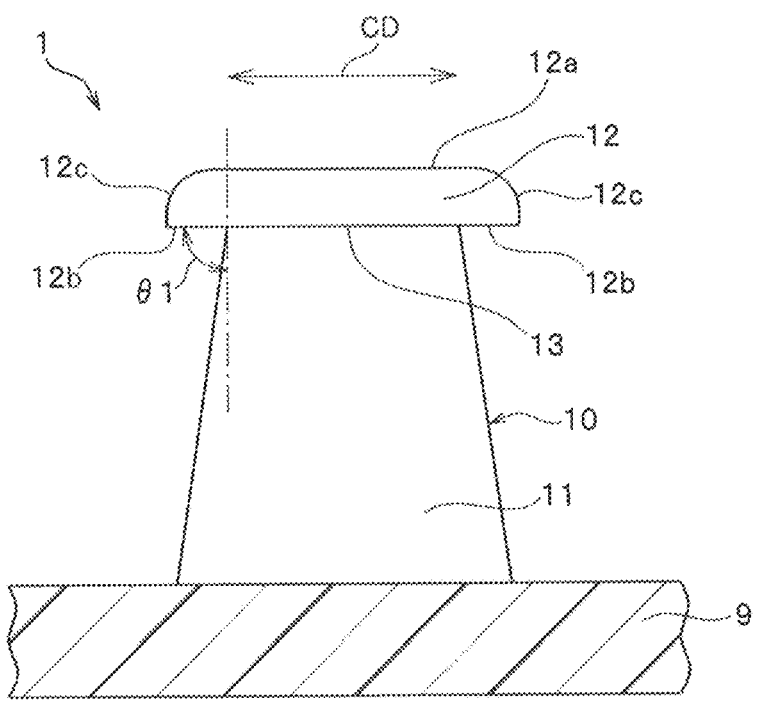
FIG. 2 is a front view of an engaging element of the molded surface fastener illustrated in FIG. 1, as viewed from a front-back direction (machine direction).
Figure 3:
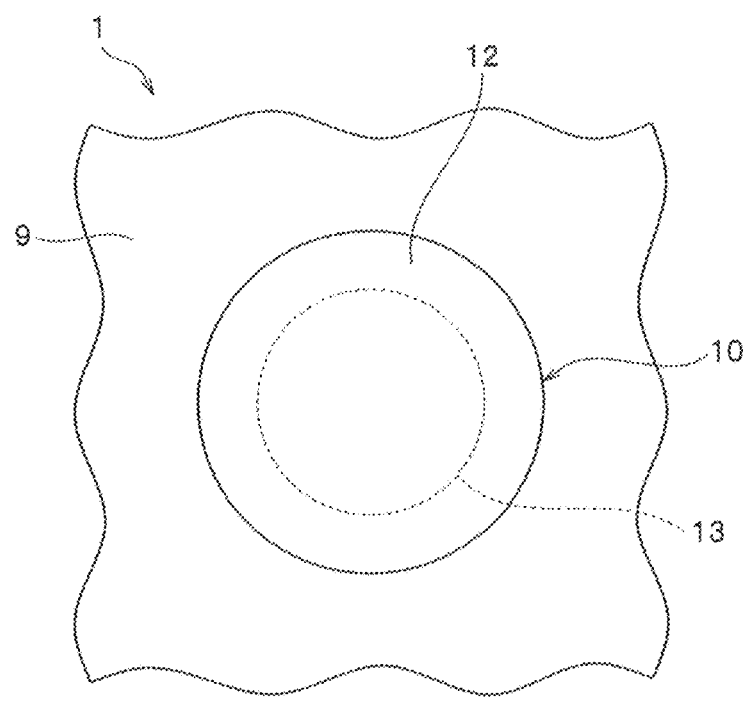
FIG. 3 is a plan view of the engaging element of the molded surface fastener illustrated in FIG. 1, as view from above.

FIG. 1 is a perspective view illustrating a molded surface fastener according to a first embodiment. FIGS. 2 and 3 are a front view and a plan view illustrating an engaging element of the first embodiment, respectively.

In the following description, the front-back direction of a molded surface fastener and a primary molded body refers to the length direction of the molded surface fastener and the primary molded body that are molded in an elongated manner as described later, and also refers to a first direction along a machine direction (MD) in which the molded surface fastener or the primary molded body is transported in the manufacturing process of the molded surface fastener.

The left-right direction refers to a width direction that is orthogonal to the length direction and is along the upper surface (or lower surface) of a base portion of the molded surface fastener. In this case, the left-right direction and the width direction can also be referred to as a cross direction (CD) or a second direction that is orthogonal to the machine direction (MD). The upper-lowerl direction (thickness direction) refers to a height direction (height direction of engaging element) that is orthogonal to the length direction and is also orthogonal to the upper surface (or lower surface) of the base portion of the molded surface fastener.

A molded surface fastener 1 according to the first embodiment is manufactured in a rectangular shape that is long in the machine direction MD of a manufacturing apparatus 20 in a plan view by using the manufacturing apparatus 20 that includes a molding device 21 and a heat-press device 28, which will be described later in FIG. 4. The length dimension (dimension in machine direction MD) and width dimension (dimension in cross direction CD) of the molded surface fastener 1 according to the invention are not particularly limited, and can be freely changed by cutting the molded surface fastener 1 or the like. Alternatively, the molded surface fastener 1 may have a shape other than a rectangle in a plan view.

The molded surface fastener 1 according to the first embodiment is made of a thermoplastic resin whose MFR and flexural modulus fall within a predetermined range, as described later. In this case, for example, a thermoplastic resin such as polypropylene, polyester, nylon, polybutylene terephthalate, or a copolymer of them can be adopted as the synthetic resin forming the molded surface fastener 1. In particular, the molded surface fastener 1 according to the first embodiment is made of polypropylene.

The molded surface fastener 1 includes a base portion 9 with a thin flat plate shape and a plurality of engaging elements 10 that stand vertically on an upper surface of the base portion 9 and have a mushroom shape. The base portion 9 is formed long along the machine direction MD at the time of manufacturing the molded surface fastener 1. In addition, the base portion 9 has a predetermined thickness that can achieve a suitable strength, and the upper surface and lower surface of the base portion 9 are formed to be flat and parallel to each other.

The engaging element 10 of the first embodiment includes a stem portion 11 standing from the base portion 9 and an engaging head portion 12 that is integrally formed on the stem portion 11 and has a disc shape or a dish shape so as to extend outward from the entire circumference of an upper end portion of the stem portion 11.

The stem portion 11 is formed so as to extend in a direction orthogonal to the upper surface of the base portion 9. Further, the stem portion 11 has a truncated cone shape in which the area of a cross-section orthogonal to the upper-lowerl direction gradually increases as approaching the base portion 9. In the invention, the shape of the stem portion 11 is not limited to a truncated cone shape, and may have, for example, a truncated pyramid shape such as a truncated square pyramid, a columnar shape, or a prism shape such as a quadrangular prism.

The engaging head portion 12 of the first embodiment is integrally formed on the stem portion 11 with a boundary portion 13 interposed between the engaging head portion 12 and the stem portion 11. This engaging head portion 12 is relatively short in vertical dimension (that is, thickness), and has a circular shape in the plan view illustrated in FIG. 3 in which the engaging element 10 is viewed from above. The circular shape of the engaging head portion 12 that can be checked in a plan view is formed to have a diameter larger than that of the circle formed by the boundary portion 13 in a plan view. In this case, the diameter of the circular engaging head portion 12 in a plan view is preferably 110% or more and 200% or less of the diameter of the circle formed by the boundary portion 13.

As illustrated in FIG. 2, the engaging head portion 12 of the first embodiment includes a flat head-portion top end surface 12a that is exposed upward, a back-side proximal end surface 12b that extends from the boundary portion 13 with the stem portion 11 toward the outside of the stem portion 11, and an outer peripheral side surface 12c that is formed in a curved surface shape that is inclined downward from an outer peripheral edge of the head-portion top end surface 12a to an outer peripheral edge of the back-side proximal end surface 12b. In this case, the head-portion top end surface 12a of the engaging head portion 12 is disposed to be parallel to the upper surface of the base portion 9, and the width dimension (width dimension of flat surface portion) in the cross direction CD of the head-portion top end surface 12a, which is formed flat, is equal to or larger than the width dimension in the cross direction CD of the stem portion 11 at the boundary portion 13. Further, the length dimension (length dimension of flat surface portion) in the machine direction MD of the head-portion top end surface 12a, which is formed flat, is equal to or larger than the length dimension in the machine direction MD of the stem portion 11 at the boundary portion 13. The outer peripheral side surface 12c with a curved surface shape is formed over the entire circumferential direction of the engaging head portion 12 between the head-portion top end surface 12a and the back-side proximal end surface 12b.

The back-side proximal end surface 12b of the engaging head portion 12 is disposed on the opposite side to the head-portion top end surface 12a in the upper-lowerl direction so as to face the base portion 9. In addition, the back-side proximal end surface 12b is formed in a donut shape or a ring shape surrounding the stem portion 11. Further, as illustrated in FIG. 2, in a front view (or rear view) when the engaging element 10 is viewed from the side of the machine direction MD, the surface of the back-side proximal end surface 12b along the cross direction CD is formed to make a back surface angle θ1 of 70° or more and 110° or less, preferably 70° or more 90° or less with respect to the height direction (upper-lowerl direction) of the stem portion 11. Here, the back surface angle θ1 refers to the angle at which the surface of the back-side proximal end surface 12b on a side of an end portion connected to the boundary portion 13 with the stem portion 11, is inclined with respect to the upper-lowerl direction.

As the back surface angle θ1 is set to 70° or more as described above, loops of a loop member such as a nonwoven fabric can easily enter the back side of the engaging head portion 12 and be easily caught. Moreover, as the back surface angle θ1 is set to 110° or less (in particular, 90° or less), in a case where the loops of the loop member are caught on the back side of the engaging head portion 12 and engaged with the back side, the engaged loops can be stably held and the loops can hardly be removed from the engaging element 10.

Particularly in the case of the first embodiment, the back surface angle θ1 of the back-side proximal end surface 12b is 90° (including error of about ±5%), and the back-side proximal end surface 12b of the engaging head portion 12 is disposed to be parallel to the upper surface of the base portion 9 and the head-portion top end surface 12a of the engaging head portion 12. In addition, the back-side proximal end surface 12b of the engaging head portion 12 is formed to make a back surface angle θ1 of 90° with respect to the upper-lowerl direction not only on the surface along the cross direction CD but also over the entire circumference of the engaging head portion 12.

Further, when the cross-section of the engaging element 10 that passes the central axis of the stem portion 11 and is orthogonal to the machine direction MD is viewed, the back-side proximal end surface 12b has a plane that shows a straight line in the range from the boundary portion 13 with the stem portion 11 to the boundary portion 13 with the outer peripheral side surface 12c. Particularly in the first embodiment, the back-side proximal end surface 12b is formed in a single flat plane shape over the entire circumference of the engaging head portion 12.

In this case, when this cross-section of the engaging element 10 is viewed, the plane portion of the back-side proximal end surface 12b is formed with a length of 20 μm or more and 90 μm or less, in particular, 40 μm or more and 90 μm or less along the cross direction CD. Since the plane portion of the back-side proximal end surface 12b has a length of 20 μm or more (in particular, 40 μm or more), loops of a loop member that is generally used in disposable diapers or the like can be easily caught on the engaging head portion 12 of the engaging element 10, and the hooked loop can be stably held by the engaging element 10. Moreover, since the plane portion of the back-side proximal end surface 12b has a length of 90 µm or less, it is possible to prevent the engaging head portion 12 from becoming too large. As a result, with respect to the formation density of the engaging element 10 for example, a space of a suitable size can be stably formed between adjacent engaging elements 10 each other.

Particularly in the case of the first embodiment, the plane portion of the back-side proximal end surface 12b is formed over the entire back-side proximal end surface 12b, and this plane portion has a length of 40 µm along the cross direction CD. Moreover, in the engaging head portion 12 of the first embodiment, the length of the plane portion of the back-side proximal end surface 12b along its radial direction is substantially the same over the entire circumference of the engaging head portion 12.

In the invention, the back-side proximal end surface 12b of the engaging head portion 12 may be formed in a curved surface shape that is curved to project along the radial direction of the engaging head portion 12. Alternatively, on the back-side proximal end surface 12b of the engaging head portion 12, for example, a portion in which the radial direction of the engaging head portion 12 is along the cross direction CD may be formed in a flat plane surface shape, and a portion in which the radial direction of the engaging head portion 12 is along the machine direction MD may be formed in a curved surface shape.

Next, a method for manufacturing the molded surface fastener 1 according to the first embodiment described above will be described.

Figure 4:
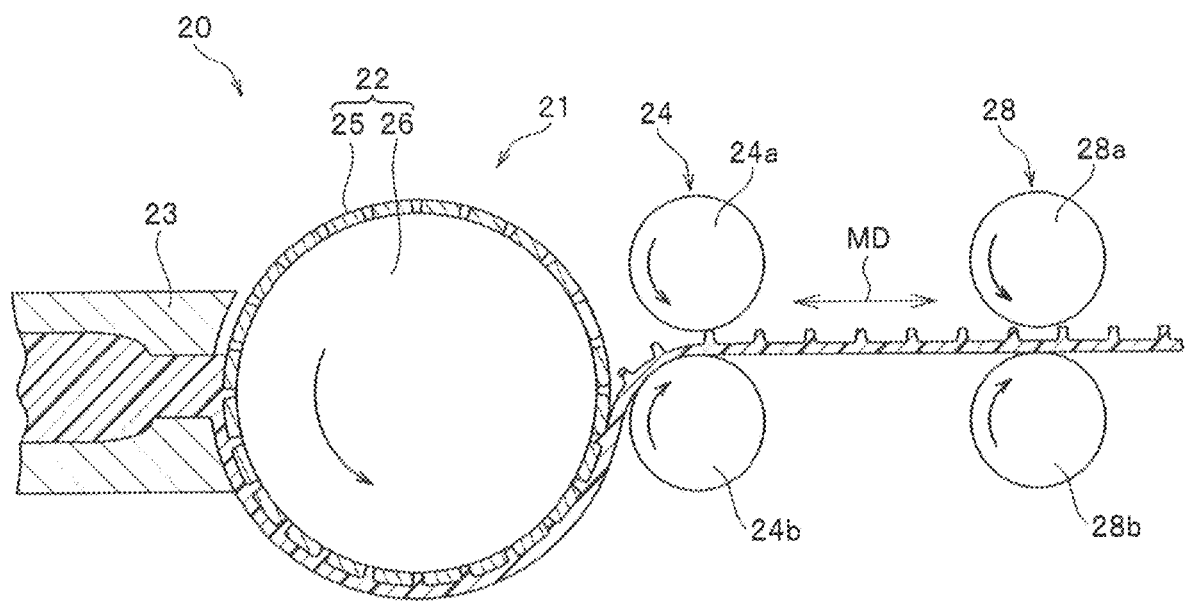
FIG. 4 is a schematic view schematically illustrating an apparatus of manufacturing a molded surface fastener according to the first embodiment.

The molded surface fastener 1 according to the first embodiment is manufactured by using the manufacturing apparatus 20 illustrated in FIG. 4. This manufacturing apparatus 20 includes the molding device 21 that performs a primary molding step and the heat-press device 28 that heats a primary molded body 1a that is molded in the primary molding step and will be described later, and presses a part of the primary molded body 1a.

The molding device 21 of the first embodiment includes a die wheel 22 that is driven to rotate in one direction (counterclockwise in FIG. 4), a nozzle portion 23 that is disposed to face a peripheral surface of the die wheel 22 and continuously pours a molten synthetic resin material into the die wheel 22, and a pickup roller 24 that is disposed on the downstream side of the nozzle portion 23 in the rotating direction of the die wheel 22.

The die wheel 22 includes a cylindrical body (sleeve) 25 that is a die member and a rotating drive roller 26 that rotates the cylindrical body 25 in one direction. A cooling jacket (not illustrated) in which a cooling liquid flows is provided inside the rotating drive roller 26, so that the primary molded body 1a that is molded on the outer peripheral surface of the die wheel 22 and will be described later can be cooled efficiently.

Figure 5:
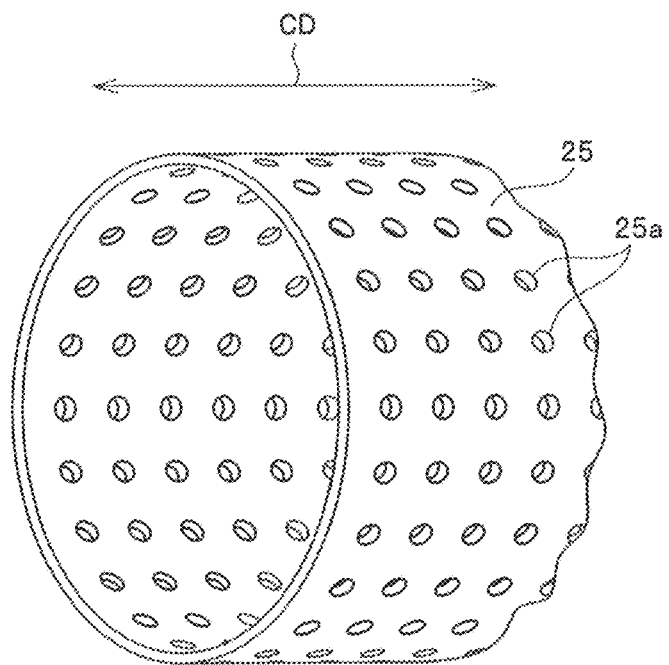
FIG. 5 is a perspective view schematically illustrating a cylindrical body that is used in a molding device of the manufacturing apparatus illustrated in FIG. 4.

As illustrated in FIG. 5, the cylindrical body 25 of the die wheel 22 has a plurality of through-holes 25a penetrating the cylindrical body 25 from the outer peripheral surface to the inner peripheral surface of the cylindrical body 25 as cavities for molding a temporary element 15 of the primary molded body 1a, which will be described later. These through-holes 25a are formed to correspond to the arrangement positions of the engaging elements 10 of the molded surface fastener 1 to be manufactured.

Further, each through-hole 25a has a truncated cone shape in which a circle formed on the outer peripheral surface of the cylindrical body 25 is larger than a circle formed on the inner peripheral surface of the cylindrical body 25. In the invention, the material and size of the cylindrical body 25 and the method for forming the cylindrical body 25 are not particularly limited.

The pickup roller 24 of the molding device 21 includes paired upper holding roller 24a and lower holding roller 24b that vertically hold and pull the primary molded body 1a molded on the outer peripheral surface portion of the die wheel 22. The upper holding roller 24a and the lower holding roller 24b are arranged so as to face each other with a predetermined distance from each other.

A surface layer (not illustrated) made of an elastomer such as a polyurethane elastomer is formed on each of the outer peripheral surface portions of the upper holding roller 24a and the lower holding roller 24b. As each of the paired upper holding roller 24a and lower holding roller 24b rotates in a predetermined direction at a predetermined speed, the primary molded body 1a can be smoothly fed to the downstream side while being continuously peeled off from the die wheel 22.

The heat-press device 28 includes paired upper pressing roller (upper calendar roller) 28a and lower pressing roller (lower calendar roller) 28b that are arranged on the downstream side of the pickup roller 24. The upper pressing roller 28a and the lower pressing roller 28b are arranged to face to each other with a predetermined distance from each other for the purpose of pressing the temporary elements 15 of the primary molded body 1a molded by the molding device 21 in the upper-lowerl direction and reducing the height dimension (dimension in upper-lowerl direction) to a predetermined dimension. In this case, the distance between the upper pressing roller 28a and the lower pressing roller 28b can be adjusted by a height adjustment unit (not illustrated).

The upper pressing roller 28a is arranged so as to rotate counterclockwise in FIG. 4. In the first embodiment, the size of the upper pressing roller 28a is not particularly limited, and the diameter (roller diameter) of the upper pressing roller 28a in a cross-section orthogonal to the rotating axis direction of the upper pressing roller 28a is freely set. Further, the upper pressing roller 28a includes a heating source (not illustrated) therein, and the outer peripheral surface of the upper pressing roller 28a heats the temporary element 15 of the primary molded body 1a at a predetermined heating temperature and at the same time, presses the temporary element 15 from above. The lower pressing roller 28b is arranged so as to rotate clockwise in FIG. 4, and supports the primary molded body 1a pressed by the upper pressing roller 28a from below.

When the molded surface fastener 1 is manufactured by using the manufacturing apparatus 20 that includes the molding device 21 and the heat-press device 28 described above, the primary molding step of molding the primary molded body 1a by the molding device 21 is performed first. In this primary molding step, a molten synthetic resin material is continuously ejected from the nozzle portion 23 toward the outer peripheral surface portion of the rotating die wheel 22.

In the primary molding step of the first embodiment, a thermoplastic resin having an MFR of 20 g/10 min or more and 60 g/10 min or less (preferably, 40 g/10 min or more and 60 g/10 min or less) and a flexural modulus of 1000 MPa or more and 2300 MPa or less (preferably, 1000 MPa or more and 1500 MPa or less) is used as the synthetic resin supplied from the nozzle portion 23 to the die wheel 22.

Since the MFR of the thermoplastic resin is 20 g/10 min or more (preferably, 40 g/10 min or more), when the upper end portion of the temporary element 15 is heated and pressed to be molded into the engaging head portion 12 in a secondary molding step to be described later, a part of the temporary element 15 can be easily softened and deformed at a predetermined heating temperature.

As a result, the engaging element 10 can be formed so that the engaging head portion 12 of the engaging element 10 is made thin and the back surface angle θ1 of the back-side proximal end surface 12b of the engaging head portion 12 falls within a predetermined range. Meanwhile, since the MFR of the thermoplastic resin is 60 g/10 min or less, it is possible to suppress the temporary element 15 from being deformed suddenly when the temporary element 15 is heated and pressed in the secondary molding step, and thus the shape of the engaging element 10 subjected to secondary molding can be stabilized.

Further, since the flexural modulus of the thermoplastic resin is 1000 MPa or more, it is possible to suppress the temporary element 15 from being deformed suddenly in the secondary molding step, and the shape of the engaging element 10 subjected to secondary molding can be stabilized. Moreover, since the rigidity of the engaging element 10 can be properly secured, it is possible to prevent the peel strength of the molded surface fastener 1 from decreasing due to the rigidity of the engaging element 10.

Meanwhile, since the flexural modulus of the thermoplastic resin is 2300 MPa or less (preferably, 1500 MPa or less), the temporary element 15 can be properly and quickly deformed at a predetermined heating temperature in the secondary molding step, and thus it is possible to stably form the engaging element 10 so that the engaging head portion 12 that is thin and flat is provided and the back surface angle θ1 of the engaging head portion 12 falls within a predetermined range. For example, in the case of the first embodiment, polypropylene having an MFR of 40 g/10 min and a flexural modulus of 1300 MPa is used as the synthetic resin forming the molded surface fastener 1.

Figure 6:
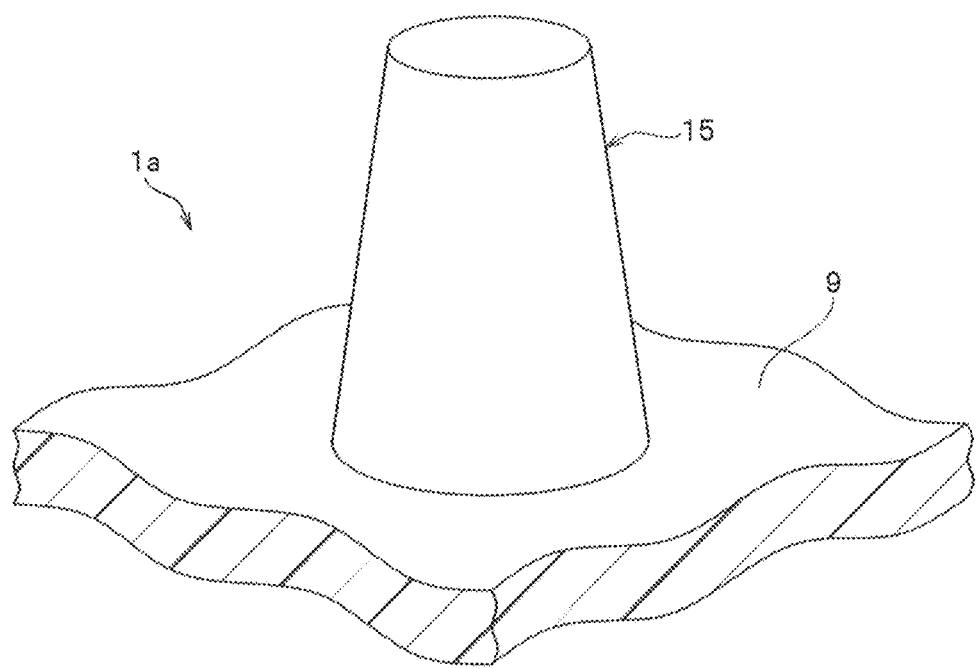
FIG. 6 is a perspective view illustrating a temporary element of a primary molded body obtained in the first embodiment.

In the primary molding step, polypropylene with the properties described above, which is in a molten state, is continuously extruded from the nozzle portion 23, and thus the primary molded body 1a in which a plurality of temporary element 15 (sometimes referred to as "temporary stem portions") illustrated in FIG. 6 are provided upright on the upper surface of the base portion 9 is molded. In this case, the base portion 9 is formed to be elongated in the machine direction between the nozzle portion 23 and the die wheel 22. At the same time, the through-holes 25a formed in the cylindrical body 25 of the die wheel 22 is filled with the thermoplastic resin, and thus the temporary elements 15 with a truncated cone shape are integrally molded with the base portion 9.

The primary molded body 1a is cured by half-rotating while being supported and cooled on the outer peripheral surface portion of the die wheel 22. Thereafter, the cured primary molded body 1a is continuously peeled off from the outer peripheral surface portion of the die wheel 22 by the pickup roller 24. In the first embodiment, the temporary element 15 of the primary molded body 1a after being peeled off from the die wheel 22 has a height dimension of 150 μm to 400 μm. Here, the height dimension of the temporary element 15 refers to the dimension in the upper-lowerl direction from the upper surface of the base portion 9 to the circular top end surface (upper end surface) of the temporary element 15.

Next, the primary molded body 1a peeled off from the die wheel 22 is transported toward the heat-press device 28 that performs the secondary molding step, and then is introduced between the upper pressing roller 28a and the lower pressing roller 28b in the heat-press device 28. In this secondary molding step, the upper pressing roller 28a heats at least the upper end portion of the temporary element 15 of the primary molded body 1a, and at the same time presses the temporary element 15 from above to crush the upper end portion of the temporary element 15.

In this case, the upper pressing roller 28a heats the temporary element 15 at a fixed heating temperature that is a first temperature or higher, the first temperature being lower than the melting point of a synthetic resin by 50° C., and a second temperature or lower, the second temperature being lower than the melting point of the synthetic resin by 20° C. By heating the temporary element 15 at the first temperature or higher, when the upper end portion of the temporary element 15 is pressed, a part of the temporary element 15 can be properly and quickly crushed and deformed.

Meanwhile, by heating the temporary element 15 at the second temperature or lower, it is possible to prevent the temporary element 15 from being deformed too much and to stably mold the engaging element 10 with a predetermined shape. For example, in the case of the first embodiment, polypropylene is used as the synthetic resin as described above, and the melting point of polypropylene is generally about 160° C. to 170° C. Consequently, in the secondary molding step of the first embodiment, the temporary element 15 is heated by the upper pressing roller 28a at a heating temperature of 110° C. or higher and 150° C. or lower. For example, in the case of the first embodiment, the heating temperature of the upper pressing roller 28a is set to 140° C.

Further, in the secondary molding step, the amount of crushing of the temporary element 15 by the heat-press device 28 (in other words, difference in height dimension between temporary element 15 and engaging element 10) is set to 20 μm or more and 80 μm or less. That is, the secondary molding step is performed so that when the height dimension of the temporary element 15 before being introduced into the heat-press device 28 is compared with the height dimension of the engaging element 10 after being molded by the heat-press device 28 from the base portion 9, the height dimension of the engaging element 10 is less than the height dimension of the temporary element 15 by 20 μm or more and 80 μm or less.

Here, the height dimension of the engaging element 10 refers to the dimension in the upper-lowerl direction from the upper surface of the base portion 9 to the flat top end surface (upper end surface) of the engaging head portion 12. In this case, the amount of crushing by the heat-press device 28 is preferably 5% or more and 40% or less of the height dimension of the temporary element 15 before being pressed. By pressing the temporary element 15 with the crushing amount described above, the characteristic engaging head portion 12 of the engaging element 10 of the first embodiment can be stably molded.

In the first embodiment, polypropylene having a predetermined MFR and flexural modulus described above is used as the material of the molded surface fastener 1, and the secondary molding step is performed under predetermined molding conditions described above. As a result, it is possible to manufacture the molded surface fastener 1 according to the first embodiment, the molded surface fastener 1 having a characteristic shape in which the engaging head portion 12 of the engaging element 10 is formed in a flat and thin shape, and the back-side proximal end surface 12b is inclined at a predetermined angle with respect to the upper-lowerl direction.

In the molded surface fastener 1 according to the first embodiment manufactured by the method described above, the back surface angle θ1 of the engaging head portion 12 is 70° or more and 110° or less, and the back-side proximal end surface 12b has a plane portion of 20 µm or more along the radial direction of the engaging head portion 12. Consequently, when a loop member such as a non-woven fabric is engaged with the molded surface fastener 1 according to the first embodiment, the loops caught on the engaging head portion 12 of the engaging element 10 can be hardly removed from the engaging element 10. As a result, the molded surface fastener 1 according to the first embodiment has a high peel strength (engagement strength) with respect to the loop member. In addition, since the top end surface of the engaging head portion 12 is formed flat in the molded surface fastener 1 according to the first embodiment, the good texture can be achieved on the upper surface side of the fastener on which a plurality of the engaging elements 10 are formed.

In the first embodiment described above, polypropylene having an MFR of 40 g/10 min and a flexural modulus of 1300 MPa is used as the synthetic resin forming the molded surface fastener 1, and the heating temperature of the upper pressing roller 28a in the secondary molding step is set to 140° C. However, in the invention, by changing the MFR and flexural modulus of the synthetic resin forming the molded surface fastener and the heating temperature of the upper pressing roller 28a within the predetermined range described above, it is possible to manufacture, for example, a molded surface fastener 2 that includes an engaging element 30 of a first modification illustrated in FIGS. 7 and 8 and a molded surface fastener 3 that includes an engaging element 40 of a second modification illustrated in FIG. 9.

For example, in the case of the first modification of the first embodiment, polypropylene having an MFR of 50 g/10 min and a flexural modulus of 1050 MPa is used as the synthetic resin forming the molded surface fastener 2. Moreover, in the secondary molding step that is performed on a primary molded body, the heating temperature of the upper pressing roller 28a is set to 130° C. Consequently, in the molded surface fastener 2 manufactured in the first modification, the overall height dimension of the engaging element 30 is less than that of the engaging element 10 of the first embodiment illustrated in FIGS. 1 to 3. In addition, in the engaging element 30 of the first modification, an engaging head portion 32 is formed thicker than the one in the first embodiment, and the diameter of the circular engaging head portion 32 of the engaging element 30 in a plan view is larger than the one in the first embodiment.

In the engaging element 30 of the first modification, the back surface angle θ1 of a back-side proximal end surface 32b of the engaging head portion 32 with respect to the upper-lowerl direction is set to 70° or more and 110° or less, specifically 90° (including error of about ±5%), similarly to the engaging element 10 of the first embodiment. Further, the back-side proximal end surface 32b of the engaging head portion 32 is formed in a single flat plane shape over the entire circumference of the engaging head portion 32. The plane portion of the back-side proximal end surface 32b has a length of 20 µm or more, specifically 50 µm along the radial direction of the engaging head portion 12.

In the molded surface fastener 2 including the engaging element 30 of the first modification, similarly to the molded surface fastener 1 of the first embodiment, the loops caught on the engaging head portion 32 of the engaging element 30 can be hardly removed from the engaging element 30, and thus the molded surface fastener 2 can have a high peel strength with respect to the loop member.

Figure 9:
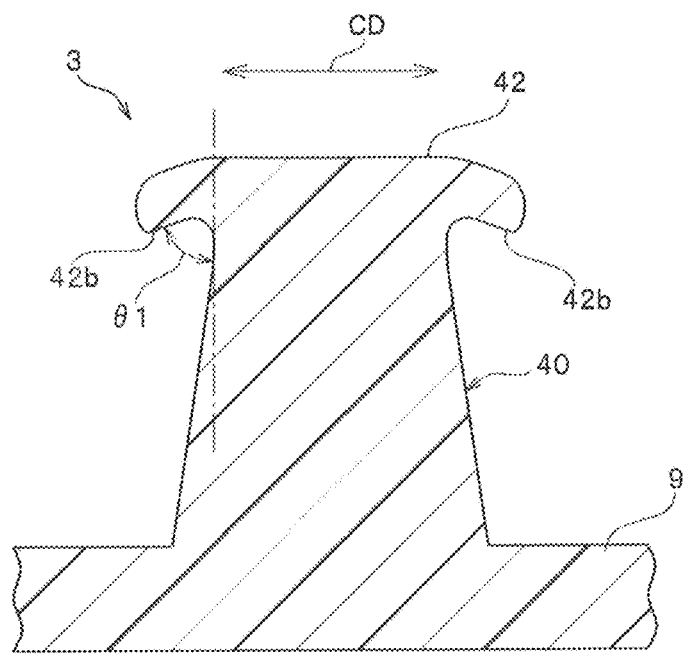
FIG. 9 is a cross-sectional view illustrating a cross-section of an engaging element of a molded surface fastener according to a second modification of the first embodiment, the cross-section being orthogonal to the front-back direction (machine direction).

In the molded surface fastener 3 according to the second modification that includes the engaging element 40 illustrated in FIG. 9, polypropylene having an MFR of 40 g/10 min or more and 60 g/10 min or less and a flexural modulus of 1000 MPa or more and 1500 MPa or less is also used as the material of the molded surface fastener 3. Further, when the molded surface fastener 3 according to the second modification is manufactured, the heating temperature of the upper pressing roller 28a is set to 110° C. or higher and 150° C. or lower in the secondary molding step.

Consequently, in the engaging element 40 of the second modification illustrated in FIG. 9, the back surface angle θ1 of a back-side proximal end surface 42b of an engaging head portion 42 with respect to the upper-lowerl direction is 70° or more and 90° or less. Moreover, when the cross-section of the engaging element 40 that is parallel to the height direction of the engaging element 40 and includes the central axis of a stem portion is viewed as illustrated in FIG. 9, the plane portion of the back-side proximal end surface 42b of the engaging head portion 42 has a length of 20 µm or more. Consequently, the molded surface fastener 3 including the engaging element 40 of the second modification can also have a high peel strength with respect to the loop member, similarly to the molded surface fastener 1 according to the first embodiment.

Second Embodiment

Figure 10:
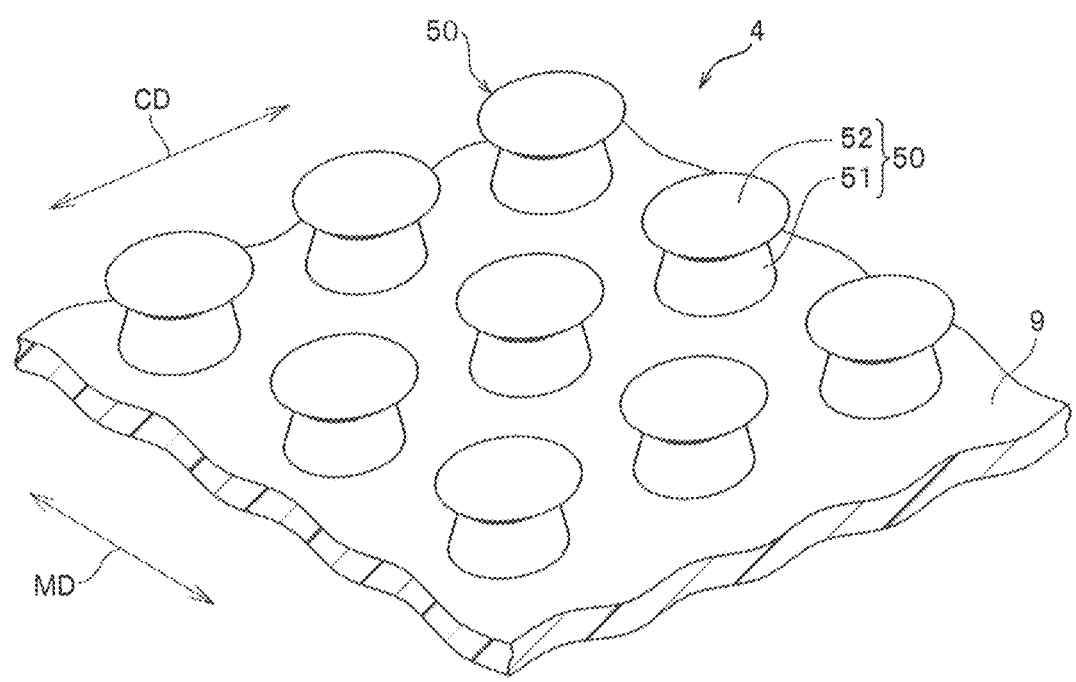
FIG. 10 is a perspective view illustrating a molded surface fastener according to a second embodiment of the invention.
Figure 11:
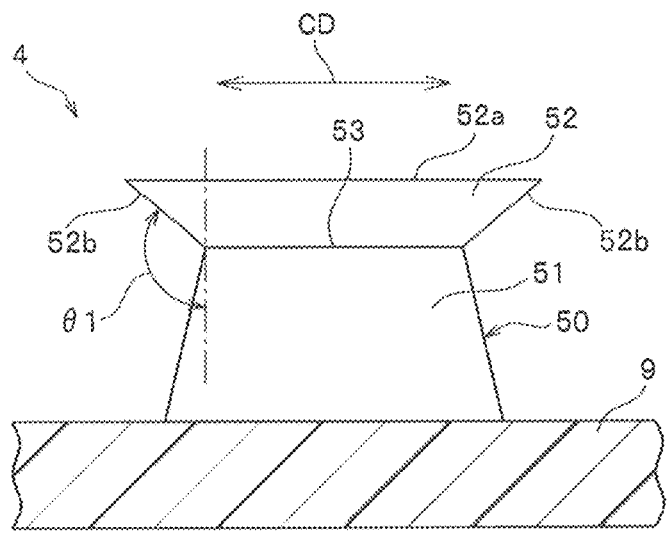
FIG. 11 is a front view of an engaging element of the molded surface fastener illustrated in FIG. 10, as viewed from the front-back direction (machine direction).
Figure 12:
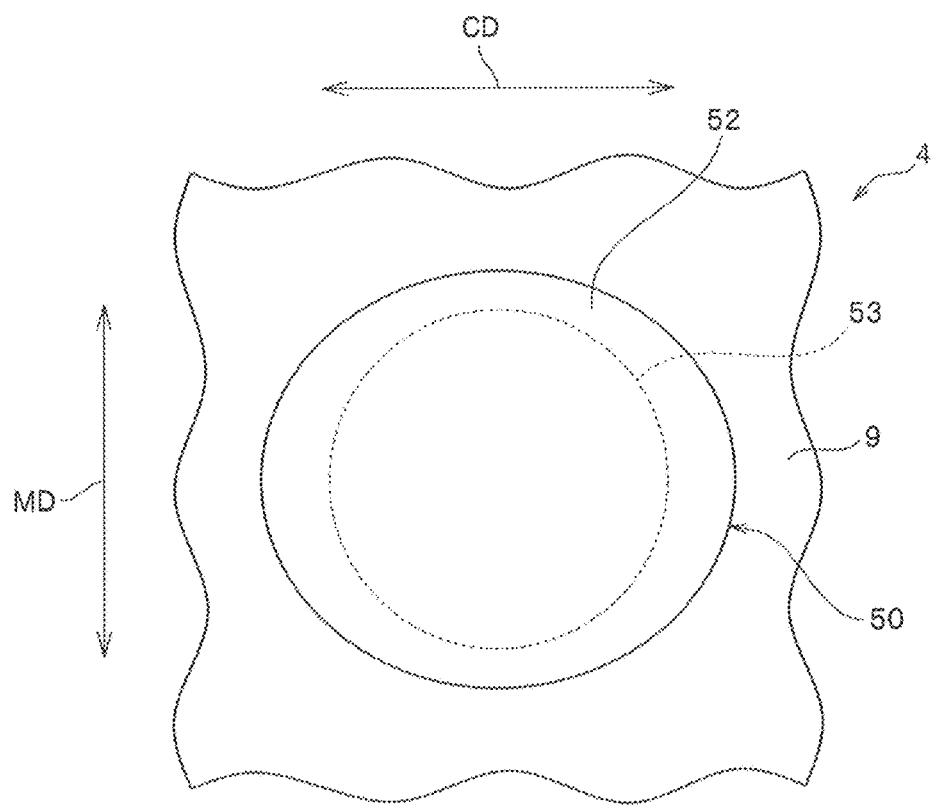
FIG. 12 is a plan view of the engaging element of the molded surface fastener illustrated in FIG. 10, as view from above.

FIG. 10 is a perspective view illustrating a molded surface fastener according to a second embodiment. FIGS. 11 and 12 are a front view and a plan view illustrating an engaging element of the second embodiment, respectively.

A molded surface fastener 4 according to the second embodiment is made of a thermoplastic resin having an MFR of 1 g/10 min or more and 60 g/10 min or less and a flexural modulus of 1600 MPa or more and 3000 MPa or less. In this case, polypropylene, polyester, nylon, polybutylene terephthalate, a copolymer of them, or the like can be used as the thermoplastic resin. Particularly in the case of the second embodiment, the molded surface fastener 4 is made of polypropylene having an MFR of 10 g/10 min and a flexural modulus of 2000 MPa, and the MFR value of polypropylene is less than the lower limit of the MFR numerical range described in the first embodiment.

The molded surface fastener 4 according to the second embodiment includes the base portion 9 with a thin flat plate shape and a plurality of engaging elements 50 that stand vertically on an upper surface of the base portion 9 and have a mushroom shape. The base portion 9 is formed similarly to the base portion 9 of the molded surface fastener 1 according to the first embodiment.

The engaging element 50 of the second embodiment includes a stem portion 51 standing from the base portion 9 and an engaging head portion 52 that is integrally formed on the stem portion 51 and is formed to extend outward from the entire circumference of an upper end portion of the stem portion 51. The stem portion 51 has a truncated cone shape in which the area of a cross-section orthogonal to the upper-lowerl direction gradually increases as approaching the base portion 9.

The engaging head portion 52 of the second embodiment is integrally formed on the stem portion 51 with a boundary portion 53 interposed between the engaging head portion 52 and the stem portion 51. The engaging head portion 52 is formed in a long elliptical shape in the cross direction CD in the plan view (FIG. 12) in which the engaging element 50 is viewed from above. In this case, in the plan view described above, the dimension of a major axis of the engaging head portion 52 along the cross direction CD is 110% or more and 200% or less, preferably 120% or more and 150% or less of the dimension of a minor axis of the engaging head portion 52 along the machine direction MD.

As illustrated in FIG. 11, the engaging head portion 52 of the second embodiment includes a head-portion top end surface 52a that is exposed upward and a back-side proximal end surface 52b that extends outward from the boundary portion 53 with the stem portion 51. The head-portion top end surface 52a of the engaging head portion 52 is formed to be flat and parallel to the upper surface of the base portion 9.

The back-side proximal end surface 52b of the engaging head portion 52 is disposed on the opposite side to the head-portion top end surface 52a in the upper-lowerl direction so as to face the base portion 9, and is formed in a ring shape surrounding the stem portion 51. Further, as illustrated in FIG. 11, in a front view when the engaging element 50 is viewed from the side of the machine direction MD, the back-side proximal end surface 52b is formed to make a back surface angle θ1 of 120° or more respect to the height direction (upper-lowerl direction) of the stem portion 51.

The molded surface fastener 4 according to the second embodiment described above is manufactured by using the manufacturing apparatus 20 that includes the molding device 21 and the heat-press device 28 illustrated in FIG. 4, as in the case of the first embodiment described above. The heat-press device 28 of the second embodiment has paired upper pressing roller 28a and lower pressing roller 28b, but a roller whose diameter (roller diameter) in a cross-section orthogonal to a rotating axis direction is 300 mm or more and 500 mm or less is used as the upper pressing roller 28a. Particularly in the case of the second embodiment, the upper pressing roller 28a has a diameter of 400 mm.

By using the upper pressing roller 28a with such a diameter, it is possible to easily and stably mold the elliptical engaging head portion 52 in which the lengths of the major axis and the minor axis have a predetermined ratio as described above from a temporary element 55 with a truncated cone shape, which will be described later. In this case, by using the upper pressing roller 28a with a larger diameter, it is possible to form the elliptical engaging head portion 52 in which the ratio of the dimension of the major axis along the cross direction CD to the dimension of the minor axis along the machine direction MD becomes larger.

Figure 13:
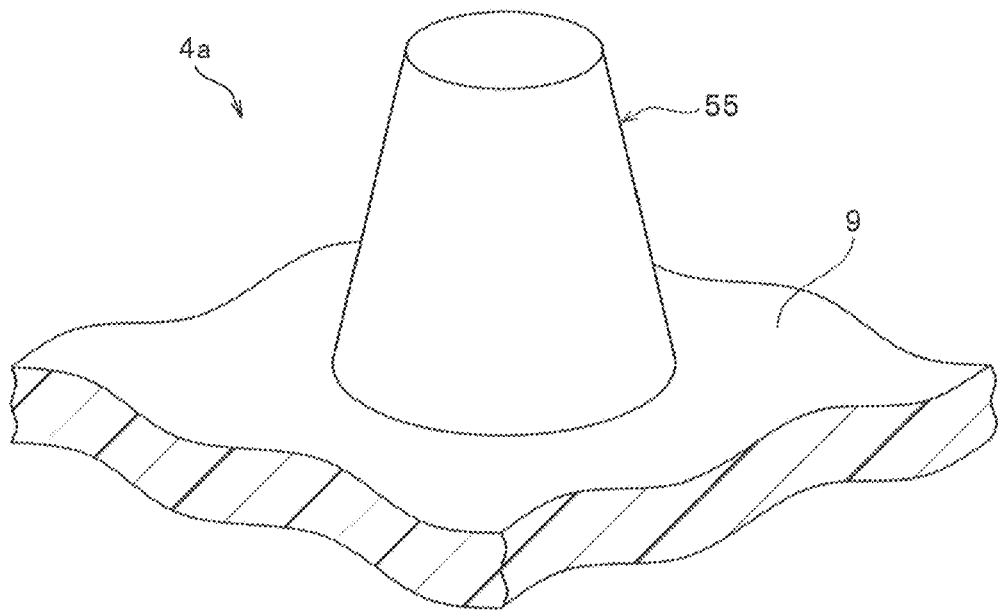
FIG. 13 is a perspective view illustrating a temporary element of a primary molded body obtained in the second embodiment.

Also in the second embodiment, the primary molding step of molding a primary molded body 4a illustrated in FIG. 13 is performed first by the molding device 21. In this case, as described above, the thermoplastic polypropylene having an MFR of 10 g/10 min and a flexural modulus of 2000 MPa is used as the synthetic resin supplied from the nozzle portion 23 to the die wheel 22. By manufacturing the molded surface fastener 4 using such a synthetic resin, the engaging element 50 in which the back surface angle θ1 of the engaging head portion 52 is 120° or more and high rigidity is achieved is molded. In addition, the engaging head portion 52 can be easily formed in an elliptical shape in the plan view of the engaging element 50.

In the second embodiment, any thermoplastic resin having an MFR of 1 g/10 min or more and 60 g/10 min or less and a flexural modulus of 1600 MPa or more and 3000 MPa or less can be selected and used as the material of the molded surface fastener 4. By performing the primary molding step and the secondary molding step as follows using the selected thermoplastic resin, it is possible to manufacture the molded surface fastener 4 according to the second embodiment in which the engaging head portion 52 has an elliptical shape in the plan view of the engaging element 50.

In the second embodiment, the primary molding step is performed similarly to the primary molding step of the first embodiment described above, except that the synthetic resin used as the material is different. As a result, the primary molded body 4a in which a plurality of temporary elements 55 illustrated in FIG. 13 are provided upright on the upper surface of the base portion 9 is molded. In this case, the temporary element 55 molded in the second embodiment has a similar shape to the temporary element 15 molded in the first embodiment described above.

Next, the primary molded body 4a obtained in the primary molding step is transported toward the heat-press device 28 that performs the secondary molding step, and then is introduced between the upper pressing roller 28a and the lower pressing roller 28b in the heat-press device 28.

In the secondary molding step of the second embodiment, the upper pressing roller 28a heats at least the upper end portion of the temporary element 55 of the primary molded body 4a, and at the same time presses the temporary element 55 from above. In this case, the upper pressing roller 28a heats the temporary element 55 at a fixed heating temperature that is a first temperature or higher, the first temperature being lower than the melting point of a synthetic resin by 50° C., and a second temperature or lower, the second temperature being lower than the melting point of the synthetic resin by 20° C., as in the case of the first embodiment described above. For example, in the case of the second embodiment, the heating temperature of the upper pressing roller 28a is set to 138° C. Further, in the secondary molding step, the amount of crushing of the temporary element 55 by the heat-press device 28 is set to 20 µm or more and 80 µm or less.

In the second embodiment, polypropylene having a predetermined MFR and flexural modulus described above is used as the material of the molded surface fastener 4, and the secondary molding step is performed under predetermined conditions using the upper pressing roller 28a with a diameter of 300 mm or more and 500 mm or less as described above. As a result, it is possible to manufacture the molded surface fastener 4 according to the second embodiment, in which the engaging head portion 52 of the engaging element 50 has a characteristic shape (that is, shape that is predetermined elliptical shape in plan view and has back surface angle θ1 of 120° or more).

In the molded surface fastener 4 according to the second embodiment manufactured by the method described above, although the back surface angle θ1 of the back-side proximal end surface 52b of the engaging head portion 52 is large, for example, 120° or more, the engaging head portion 52 has an elliptical shape in the plan view of the engaging element 50. Further, the molded surface fastener 4 is made of polypropylene having a high flexural modulus, for example, a flexural modulus of 2000 MPa, and the rigidity of each engaging element 50 is enhanced. Consequently, when a loop member such as a non-woven fabric is engaged with the molded surface fastener 4 according to the second embodiment, the state where the loops are engaged with the engaging element 50 can be easily and stably maintained, and the loops caught on the elliptical engaging head portion 52 of the engaging element 50 can be hardly removed from the engaging element 50.

As a result, the molded surface fastener 4 according to the second embodiment has a high peel strength (engagement strength) with respect to the loop member. In addition, in the molded surface fastener 4 according to the second embodiment, the flat head-portion top end surface 52a of the engaging head portion 52 is more likely to be formed wider than the one in the molded surface fastener 1 according to the first embodiment described above, and thus a better texture on the upper surface side of the fastener can be achieved.

EXAMPLES

Hereinafter, the invention will be described in more detail with reference to examples.

First Example

As a first example, the molded surface fastener 1 illustrated in FIGS. 1 to 3 was manufactured under the conditions described in the first embodiment described above. That is, the molded surface fastener 1 according to the first example was manufactured by using polypropylene having an MFR of 40 g/10 min and a flexural modulus of 1300 MPa as the synthetic resin forming the molded surface fastener 1 and setting the heating temperature of the upper pressing roller 28a in the secondary molding step to 140° C.

In the molded surface fastener 1 manufactured in the first example, the back surface angle θ1 of the back-side proximal end surface 12b along the radial direction of the engaging head portion 12 and the cross direction CD is 90°, and the back-side proximal end surface 12b has a plane portion of 40 μm along the radial direction of the engaging head portion 12.

Second Example

Figure 7:
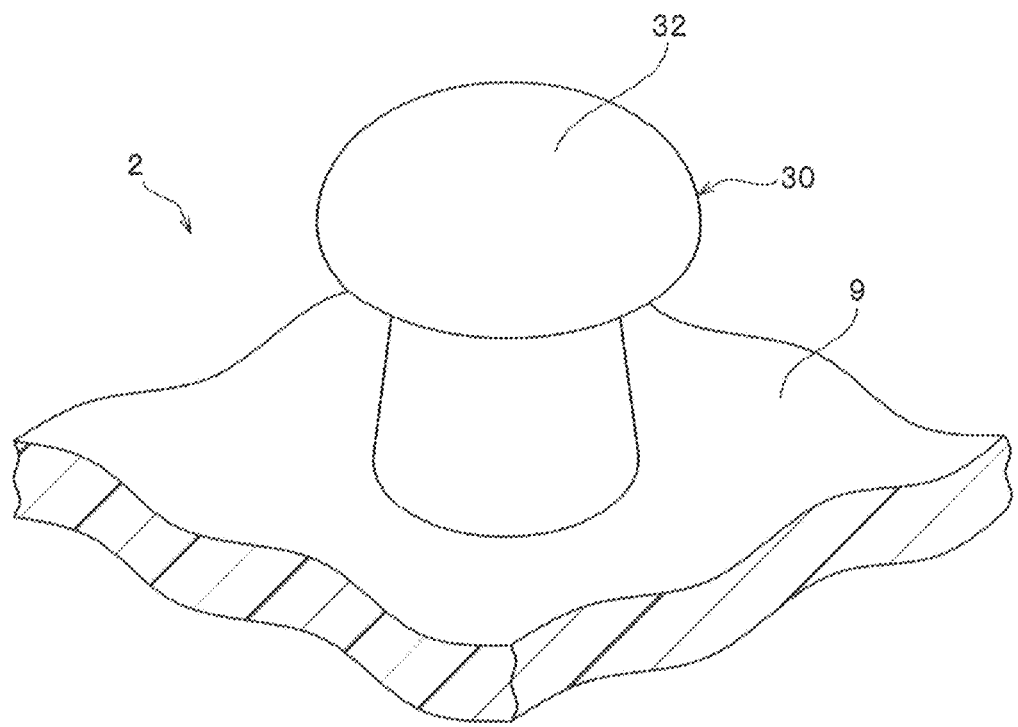
FIG. 7 is a perspective view illustrating an engaging element of a molded surface fastener according to a first modification of the first embodiment.
Figure 8:
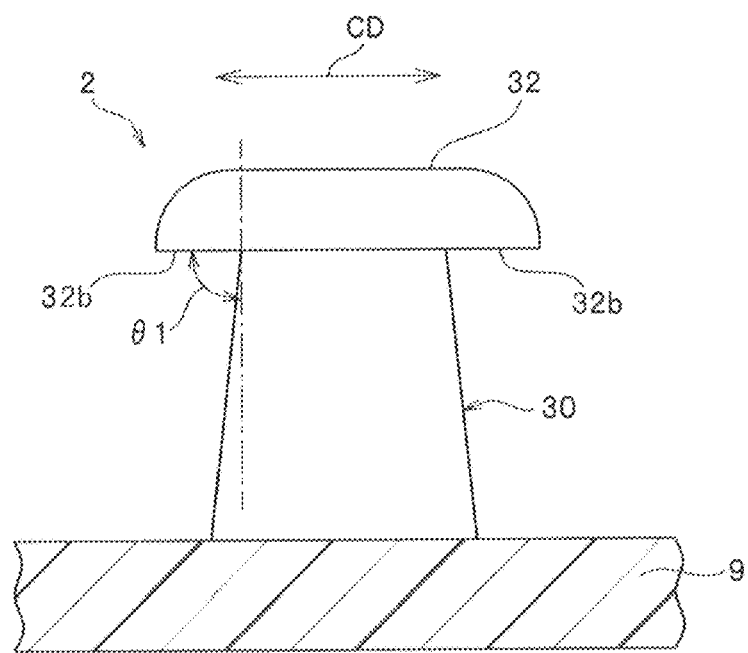
FIG. 8 is a front view of the engaging element illustrated in FIG. 7, as viewed from the front-back direction (machine direction).

As a second example, the molded surface fastener 2 illustrated in FIGS. 7 and 8 was manufactured under the conditions described in the first modification of the first embodiment described above. That is, the molded surface fastener 2 according to the second example was manufactured by using polypropylene having an MFR of 50 g/10 min and a flexural modulus of 1050 MPa as the synthetic resin forming the molded surface fastener 2 and setting the heating temperature of the upper pressing roller 28a in the secondary molding step to 130° C.

In the molded surface fastener 2 manufactured in the second example, the back surface angle θ1 of the back-side proximal end surface 32b along the radial direction of the engaging head portion 32 and the cross direction CD is 90°, and the back-side proximal end surface 32b has a plane portion of 50 μm along the radial direction of the engaging head portion 32.

First Comparative Example

Figure 14:
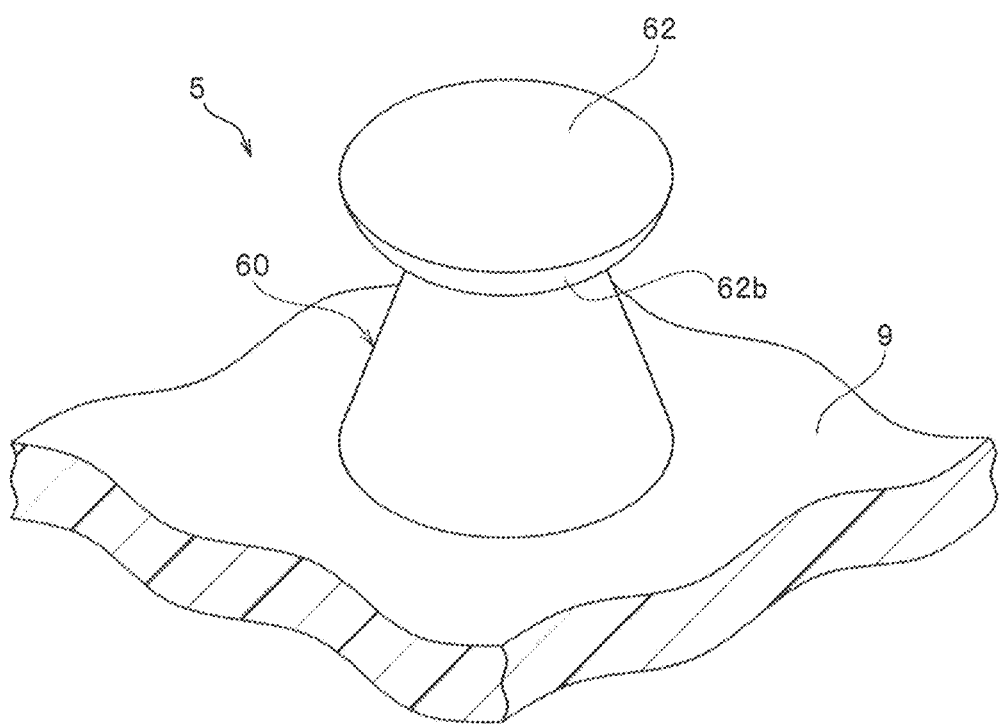
FIG. 14 is a perspective view illustrating an engaging element of a molded surface fastener according to a first comparative example.
Figure 15:
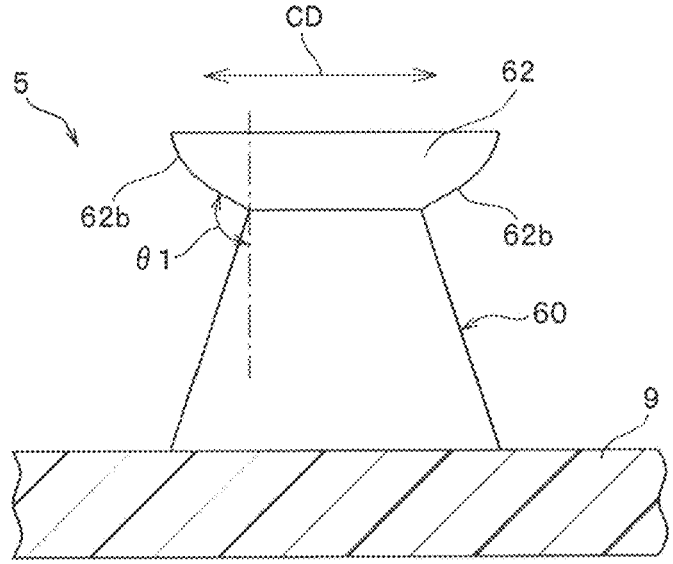
FIG. 15 is a front view of the engaging element illustrated in FIG. 14, as viewed from the front-back direction (machine direction).

In a first comparative example, the molded surface fastener 5 according to the first comparative example illustrated in FIGS. 14 and 15 was manufactured in a manner that a molded surface fastener was manufactured by using polypropylene having an MFR of 10 g/10 min and a flexural modulus of 2000 MPa as the synthetic resin and setting the heating temperature of the upper pressing roller 28a in the secondary molding step to 130° C. Conditions other than the MFR and flexural modulus of polypropylene and the heating temperature of the upper pressing roller 28a were set similarly to those of the first example (first embodiment).

The molded surface fastener 5 manufactured in the first comparative example had a plurality of engaging elements 60 illustrated in FIGS. 14 and 15. Further, in the case of the first comparative example, the back surface angle θ1 of a back-side proximal end surface 62b along the radial direction of an engaging head portion 62 and the cross direction CD was 120°. Moreover, a plane portion was not formed on the back-side proximal end surface 62b of the engaging head portion 62 (that is, length of plane portion on back-side proximal end surface 62b of engaging head portion 62 along radial direction on was 0 μm).

Third Example

As a third example, the molded surface fastener 4 illustrated in FIGS. 10 to 12 was manufactured under the conditions described in the second embodiment described above. That is, polypropylene having an MFR of 10 g/10 min and a flexural modulus of 2000 MPa was used as the synthetic resin forming the molded surface fastener 4. Further, the molded surface fastener 4 according to the third example was manufactured by using the upper pressing roller 28a with a diameter of 400 mm and setting the heating temperature of the upper pressing roller 28a to 138° C. in the secondary molding step.

In the molded surface fastener 4 manufactured in the third example, the back surface angle θ1 of the back-side proximal end surface 52b along the radial direction of the engaging head portion 52 and the cross direction CD was 120° or more. Further, the engaging head portion 52 had a long elliptical shape in the cross direction CD in the plan view of the engaging element 50, and the dimension of the major axis of the engaging head portion 52 along the cross direction CD was 122% of the dimension of the minor axis of the engaging head portion 52 along the machine direction MD.

Second Comparative Example

In a second comparative example, the same polypropylene as that used in the third example, that is, polypropylene having an MFR of 10 g/10 min and a flexural modulus of 2000 MPa was used as the synthetic resin. Further, a molded surface fastener 6 according to the second comparative example illustrated in FIGS. 16 to 18 was manufactured by using the upper pressing roller 28a with a diameter of 100 mm and setting the heating temperature of the upper pressing roller 28a to 135° C. in the secondary molding step. Conditions other than the diameter and heating temperature of the upper pressing roller 28a were set similarly to those of the third example (second embodiment).

Figure 16:
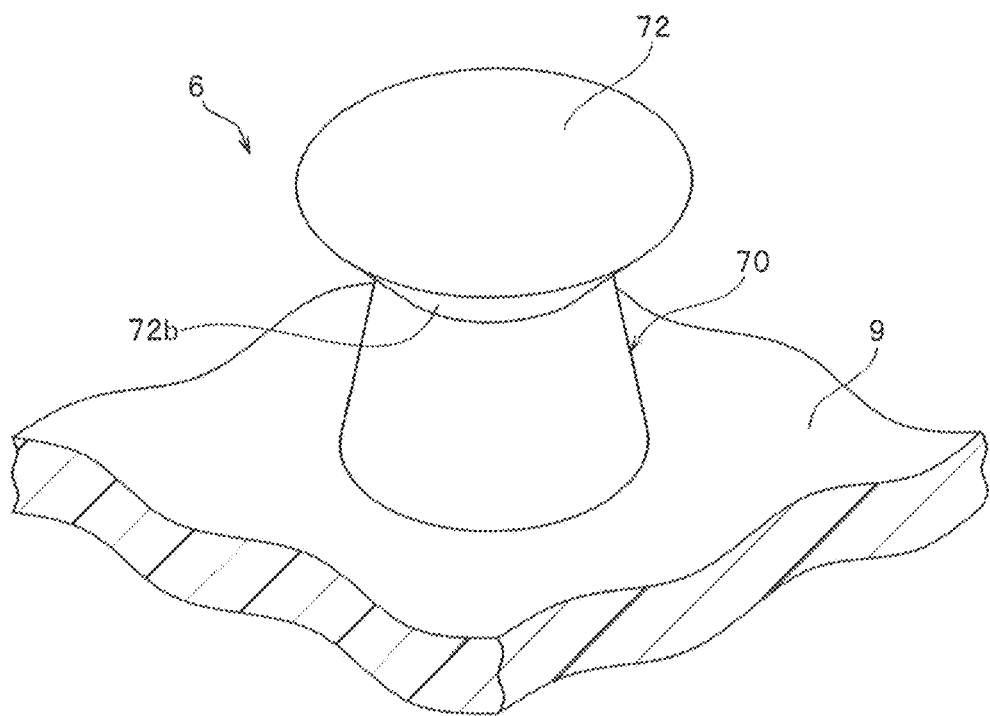
FIG. 16 is a perspective view illustrating an engaging element of a molded surface fastener according to a second comparative example.
Figure 17:
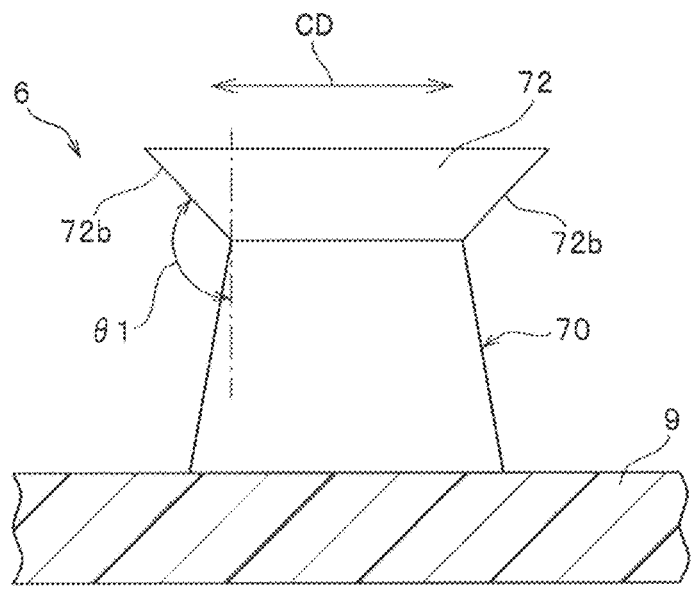
FIG. 17 is a front view of the engaging element illustrated in FIG. 16, as viewed from the front-back direction (machine direction).
Figure 18:
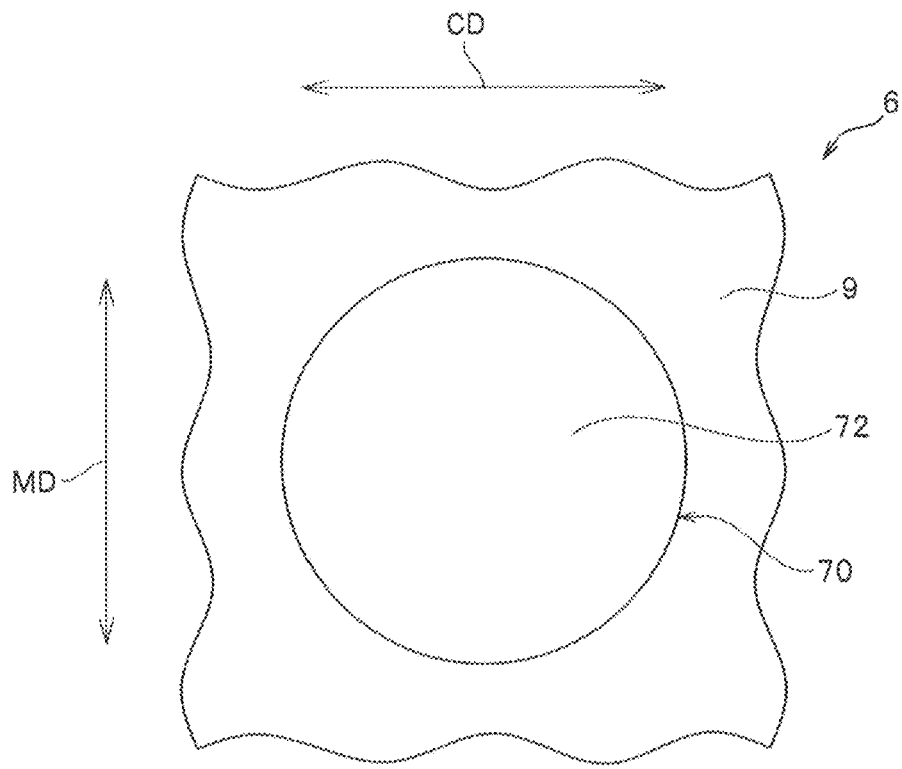
FIG. 18 is a plan view of the engaging element illustrated in FIG. 16, as viewed from above.

The molded surface fastener 6 manufactured in the second comparative example had a plurality of engaging elements 70 illustrated in FIGS. 16 to 18. In the case of the second comparative example, the back surface angle θ1 of a back-side proximal end surface 72b along the radial direction of an engaging head portion 72 and the cross direction CD was 120° or more. Further, the engaging head portion 72 had a circular shape in the plan view of the engaging element 70, and the dimension of the engaging head portion 72 along the cross direction CD was 98% of the dimension of the engaging head portion 72 along the machine direction MD.

After the molded surface fasteners 1, 2, 4, 5, and 6 according to the first to third examples and the first and second comparative examples were manufactured respectively, a test to measure the peel strength was performed on the obtained molded surface fasteners 1, 2, 4, 5, and 6.

Figure 19:
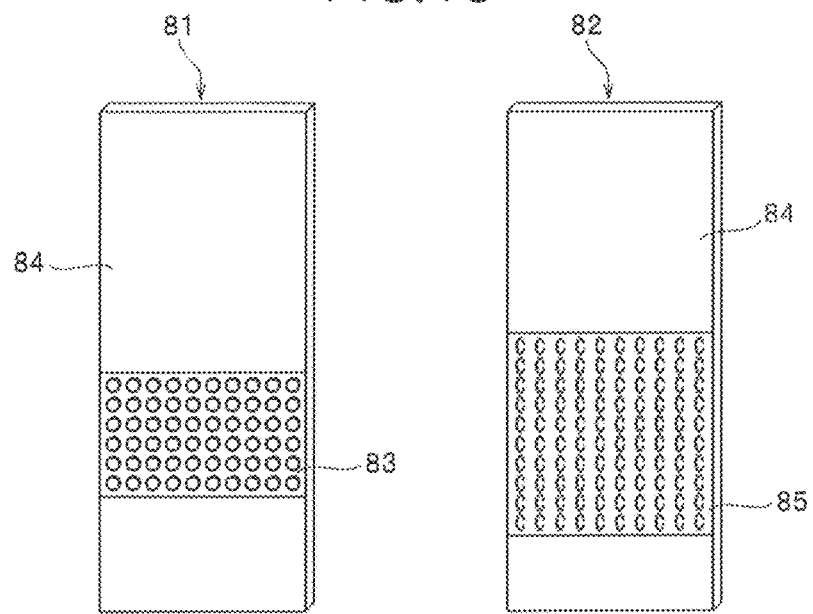
FIG. 19 is a view illustrating test pieces used for a peel strength test of a surface fastener.

In this peel strength test, as illustrated in FIG. 19, each of the molded surface fasteners 1, 2, 4, 5, and 6 according to the first to third examples and the first and second comparative examples was cut in a size of 25 mm in the machine direction MD×25 mm in the cross direction CD. A cut piece 83 of the molded surface fastener cut was then adhesively fixed to a support member 84 made of a non-woven fabric, so that a first test piece 81 on a molded surface fastener side was prepared. In addition, a non-woven fabric 85 larger in size in the machine direction MD than the cut piece 83 of the molded surface fastener was adhesively fixed to the support member 84, so that a second test piece 82 on a loop member side was prepared.

Figure 20:
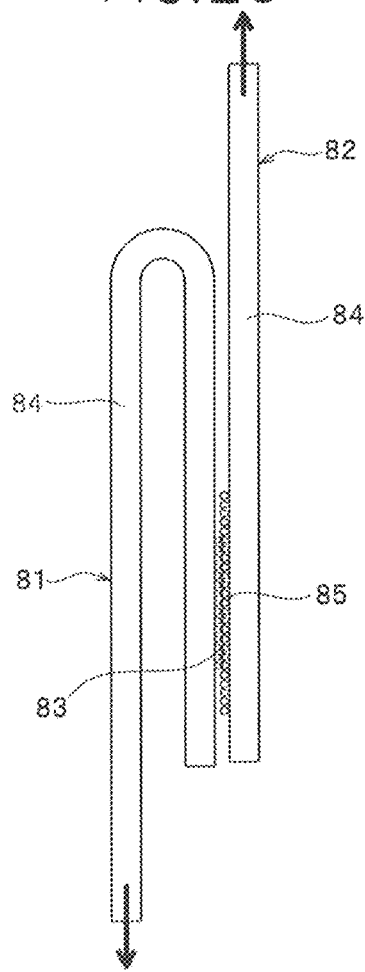
FIG. 20 is an explanatory view for explaining the peel strength test.

Next, as illustrated in FIG. 20, the cut piece 83 of the molded surface fastener on the first test piece 81 was engaged with the second test piece 82. Subsequently, the first test piece 81 and the second test piece 82 were each gripped by paired clampers (not illustrated), and then the paired clampers gripping the first test piece 81 and the second test piece 82 were moved at a constant speed so as to be separated from each other, so that a load was gradually applied to the first test piece 81 and the second test piece 82 in an engaged state. The peel strength of each of the molded surface fasteners 1, 2, 4, 5, and 6 was determined by measuring the load when the engaged state was released.

Such a peel strength test was performed for a plurality of times on each of the molded surface fasteners 1, 2, 4, 5, and 6 according to the first to third examples and the first and second comparative examples, and the average value of the peel strength measured was calculated. The following Table 1 and Table 2 show the average value of the peel strength calculated for each of the molded surface fasteners 1, 2, 4, 5, and 6, together with the manufacturing conditions of each of the molded surface fasteners 1, 2, 4, 5, and 6 and numerical values related to the shape of the engaging head portion.

TABLE 1

|  | First example | Second example | First comparative example |
| --- | --- | --- | --- |
| MFR (g/10 min) | 40 | 50 | 10 |
| Flexural modulus (MPa) | 1300 | 1050 | 2000 |
| Heating temperature in secondary molding step (° C.) | 140 | 130 | 130 |
| Back surface angle θ1 (°) | 90 | 90 | 120 |
| Length of plane portion of back-side — proximal end surface (μm) | 40 | 50 | 0 |
| Peel strength (N/cm) | 0.6 | 0.56 | 0.15 |

TABLE 2

|  | Third example | Second comparative example |
| --- | --- | --- |
| MFR(g/10 min) | 10 | 10 |
| Flexural modulus(MPa) | 2000 | 2000 |
| Heating temperature in secondary molding step (° C.) | 138 | 135 |
| Ratio of major axis to minor axis of ellipse | 1.22 | 0.98 |
| Diameter of upper pressing roller(mm) | 400 | 100 |
| Peel strength(N/cm) | 0.53 | 0.09 |

As shown in Table 1, it has been appeared that the molded surface fasteners 1 and 2 according to the first and second examples have a peel strength three times or more higher than that of the molded surface fastener 5 according to the first comparative example. In addition, as shown in Table 2, it has been appeared that the molded surface fastener 4 according to the third example has a peel strength five times or more higher than that of the molded surface fastener 6 according to the second comparative example.

The first embodiment and the second embodiment described above describe the case where the primary molding step of the molded surface fastener is performed by using the molding device 21 having the die wheel 22 illustrated in FIG. 4. However, it is also possible in the invention to use other forms of the molding device in the primary molding step of the molded surface fastener.

For example, it is possible to use, as a molding device that molds a primary molded body, a molding device (so-called twin wheel or twin roll molding device) that includes a die wheel that is driven to rotate in one direction, a press wheel that is arranged with a predetermined distance between the press wheel and the die wheel and that is driven to rotate in the opposite direction to the die wheel, and a nozzle portion that pours a molten synthetic resin between the die wheel and the press wheel.

In this case, the die wheel disposed in the twin wheel molding device has the structure similar to that of the die wheel 22 illustrated in FIG. 4, which is used in the first embodiment described above. By performing the primary molding step using the twin wheel molding device having these die wheel and press wheel, the molded surface fastener according to the first embodiment or the second embodiment described above can also be stably manufactured.

REFERENCE SIGNS LIST

1 Molded surface fastener
1a Primary molded body
2, 3 Molded surface fastener
4 Molded surface fastener
4a Primary molded body
5, 6 Molded surface fastener
9 Base portion
10 Engaging element
11 Stem portion
12 Engaging head portion
12a Head-portion top end surface
12b Back-side proximal end surface
12c Outer peripheral side surface
13 Boundary portion
15 Temporary element
20 Manufacturing apparatus
21 Molding device
22 Die wheel
23 Nozzle portion
24 Pickup roller
24a Upper holding roller
24b Lower holding roller
25 Cylindrical body (sleeve)
25a Through-hole
26 Rotating drive roller
28 Heat-press device
28a Upper pressing roller (upper calendar roller)
28b Lower pressing roller (lower calendar roller)
30 Engaging element
32 Engaging head portion
32b Back-side proximal end surface
40 Engaging element
42 Engaging head portion
42b Back-side proximal end surface
50 Engaging element
51 Stem portion 52 Engaging head portion
52a Head-portion top end surface
52b Back-side proximal end surface
53 Boundary portion
55 Temporary element
60 Engaging element
62 Engaging head portion
62b Back-side proximal end surface
70 Engaging element
72 Engaging head portion
72b Back-side proximal end surface
81 First test piece
82 Second test piece
83 Cut piece
84 Support member
85 Non-woven fabric
CD Cross direction
MD Machine direction
θ1 Back surface angle

The invention claimed is:

1. A method for manufacturing a molded surface fastener that is made of a synthetic resin and has a plurality of engaging elements each of which includes a stem portion standing from a base portion and an engaging head portion integrally formed on the stem portion, the method including a primary molding step of molding a primary molded body having the base portion and a plurality of temporary elements provided upright on the base portion and a secondary molding step of heating at least a part of each of the temporary elements of the primary molded body and pressing the temporary elements from above to mold the molded surface fastener, wherein
the method comprises using a thermoplastic resin having a melt flow rate of 20 g/10 min or more and 60 g/10 min or less and a flexural modulus of 1000 MPa or more and 2300 MPa or less as the synthetic resin.

2. A method for manufacturing a molded surface fastener that is made of a synthetic resin and has a plurality of engaging elements each of which includes a stem portion standing from a base portion and an engaging head portion integrally formed on the stem portion, the method including a primary molding step of molding a primary molded body having the base portion and a plurality of temporary elements provided upright on the base portion and a secondary molding step of heating at least a part of each of the temporary elements of the primary molded body and pressing the temporary elements from above to mold the molded surface fastener, wherein
the method comprises using a thermoplastic resin having a melt flow rate of 1 g/10 min or more and 60 g/10 min or less and a flexural modulus of 1600 MPa or more and 3000 MPa or less as the synthetic resin, and
pressing the temporary elements from above by a pressing roller with a diameter of 300 mm or more and 500 mm or less in the secondary molding step.

3. The method for manufacturing a molded surface fastener according to claim 1, wherein the method comprises molding the engaging element whose height dimension is less than the height dimension of the temporary element by 20 μm or more and 80 μm or less by heating at least a part of the temporary element at a heating temperature that is a first temperature or higher, the first temperature being lower than a melting point of the synthetic resin by 50° C., and a second temperature or lower, the second temperature being lower than the melting point of the synthetic resin by 20° C., and pressing the temporary element from above in the secondary molding step.

4. A molded surface fastener that is made of a synthetic resin and has a plurality of engaging elements each of which includes a stem portion standing from a base portion and an engaging head portion integrally formed on the stem portion, wherein
the engaging head portion has at least a top end surface that is exposed upward and formed flat and a back-side proximal end surface that is disposed on an opposite side to the top end surface and extends outward from a boundary portion with the stem portion, and
at least a part of the back-side proximal end surface of the engaging head portion has an angle of 70° or more and 110° or less with respect to a height direction of the stem portion.

5. The molded surface fastener according to claim 4, wherein
the engaging head portion has a circular shape in a plan view of the molded surface fastener,
at least a part of the back-side proximal end surface of the engaging head portion has a plane that shows a straight line when a cross-section that is parallel to a height direction of the engaging element and includes a central axis of the stem portion is viewed in the engaging element, and
the plane of the back-side proximal end surface has a length of 20 μm or more in the cross-section.

6. A molded surface fastener that is made of a synthetic resin and has a plurality of engaging elements each of which includes a stem portion standing from a base portion and an engaging head portion integrally formed on the stem portion, wherein
the engaging head portion has at least a top end surface that is exposed upward and a back-side proximal end surface that is disposed on an opposite side to the top end surface and extends outward from a boundary portion with the stem portion, and the engaging head portion has an elliptical shape in a plan view of the molded surface fastener, and
at least a part of the back-side proximal end surface of the engaging head portion has an angle of 120° or more with respect to a height direction of the stem portion.

7. The method for manufacturing a molded surface fastener according to claim 2, wherein the method comprises molding the engaging element whose height dimension is less than the height dimension of the temporary element by 20 μm or more and 80 μm or less by heating at least a part of the temporary element at a heating temperature that is a first temperature or higher, the first temperature being lower than a melting point of the synthetic resin by 50° C., and a second temperature or lower, the second temperature being lower than the melting point of the synthetic resin by 20° C., and pressing the temporary element from above in the secondary molding step.

* * * * *

UNITED STATES PATENT AND TRADEMARK OFFICE
CERTIFICATE OF CORRECTION

| | |
|---|---|
| PATENT NO. | : 11,819,091 B2 |
| APPLICATION NO. | : 17/291146 |
| DATED | : November 21, 2023 |
| INVENTOR(S) | : Yoshiyuki Fukuhara et al. |

It is certified that error appears in the above-identified patent and that said Letters Patent is hereby corrected as shown below:

In the Specification

In Column 6, Line 1, delete "upper-lowerl" and insert -- upper-lower --.

In Column 6, Line 6, delete "(upper-lowerl" and insert -- (upper-lower --.

In Column 6, Line 12, delete "upper-lowerl" and insert -- upper-lower --.

In Column 6, Line 58, delete "upper-lowerl" and insert -- upper-lower --.

In Column 6, Line 64, delete "(upper-lowerl" and insert -- (upper-lower --.

In Column 7, Line 2, delete "upper-lowerl" and insert -- upper-lower --.

In Column 8, Line 47, delete "upper-lowerl" and insert -- upper-lower --.

In Column 9, Lines 26-27, delete "upper-lowerl" and insert -- upper-lower --.

In Column 10, Line 8, delete "upper-lowerl" and insert -- upper-lower --.

In Column 10, Line 18, delete "(upper-lowerl" and insert -- (upper-lower --.

In Column 10, Line 23, delete "upper-lowerl" and insert -- upper-lower --.

In Column 10, Line 43, delete "upper-lowerl" and insert -- upper-lower --.

In Column 12, Line 28, delete "upper-lowerl" and insert -- upper-lower --.

In Column 12, Line 29, delete "upper-lowerl" and insert -- upper-lower --.

Signed and Sealed this
Twenty-seventh Day of February, 2024

Katherine Kelly Vidal
*Director of the United States Patent and Trademark Office*

In Column 13, Lines 59-60, delete "upper-lowerl" and insert -- upper-lower --.

In Column 14, Line 44, delete "upper-lowerl" and insert -- upper-lower --.

In Column 14, Lines 64-65, delete "upper-lowerl" and insert -- upper-lower --.

In Column 15, Line 52, delete "upper-lowerl" and insert -- upper-lower --.

In Column 16, Line 14, delete "upper-lowerl" and insert -- upper-lower --.

In Column 16, Line 59, delete "upper-lowerl" and insert -- upper-lower --.

In Column 17, Line 16, delete "upper-lowerl" and insert -- upper-lower --.

In Column 17, Line 23, delete "(upper-lowerl" and insert -- (upper-lower --.